United States Patent
Mitsuyama et al.

(10) Patent No.: US 9,110,019 B2
(45) Date of Patent: Aug. 18, 2015

(54) ANALYTICAL APPARATUS AND ANALYTICAL METHOD

(75) Inventors: Satoshi Mitsuyama, Tokyo (JP); Norio Owada, Naka (JP); Chihiro Manri, Kawagoe (JP); Sadamitsu Aso, Kawasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 26 days.

(21) Appl. No.: 13/809,098

(22) PCT Filed: Jul. 8, 2011

(86) PCT No.: PCT/JP2011/003917
§ 371 (c)(1),
(2), (4) Date: Jan. 8, 2013

(87) PCT Pub. No.: WO2012/008129
PCT Pub. Date: Jan. 19, 2012

(65) Prior Publication Data
US 2013/0107256 A1    May 2, 2013

(30) Foreign Application Priority Data

Jul. 14, 2010  (JP) ................. 2010-159279

(51) Int. Cl.
*G01J 3/28* (2006.01)
*G01N 21/53* (2006.01)
*G01N 15/10* (2006.01)
*G01N 15/14* (2006.01)
(Continued)

(52) U.S. Cl.
CPC ............ *G01N 21/53* (2013.01); *G01N 15/1012* (2013.01); *G01N 15/1459* (2013.01); *G01N 21/25* (2013.01); *G01N 21/64* (2013.01)

(58) Field of Classification Search
CPC .............. G01N 2021/6421; G01N 2021/6441; G01N 2021/6419; G01N 21/645; G01N 21/6458; G01N 2021/7786; G01N 2021/6417
USPC ................................................ 356/328, 300
See application file for complete search history.

(56) References Cited

U.S. PATENT DOCUMENTS

| 6,730,521 B1 | 5/2004 | Cassells |
| 2002/0006631 A1 | 1/2002 | Houwen et al. |
| 2003/0215791 A1* | 11/2003 | Garini et al. ............ 435/5 |

(Continued)

FOREIGN PATENT DOCUMENTS

| JP | 61-1 731 41 A | 8/1986 |
| JP | 4-65654 A | 3/1992 |

(Continued)

OTHER PUBLICATIONS

International Search Report with English translation dated Oct. 4, 2011 (six (6) pages).

*Primary Examiner* — Tarifur Chowdhury
*Assistant Examiner* — Sunghee Y Gray
(74) *Attorney, Agent, or Firm* — Crowell & Moring LLP

(57) ABSTRACT

Disclosed is a flow cytometer using a spectral device and a multi-detector, in which setting of an optimum wavelength band prior to measuring fluorescence intensity in real time is supported. A signal processing unit stores the intensities in multiple wavelength bands, the intensities being obtained by measuring a calibration sample, and the distribution of the intensities is calculated and displayed by each of the wavelength bands.

4 Claims, 22 Drawing Sheets

(51) Int. Cl.
*G01N 21/25* (2006.01)
*G01N 21/64* (2006.01)

(56) References Cited

U.S. PATENT DOCUMENTS

| | | | |
|---|---|---|---|
| 2005/0064427 A1 | 3/2005 | Gluch et al. | |
| 2006/0273260 A1* | 12/2006 | Casstevens et al. | 250/458.1 |
| 2009/0012721 A1* | 1/2009 | Kimura et al. | 702/23 |
| 2010/0032568 A1* | 2/2010 | Fraser et al. | 250/336.2 |
| 2011/0312511 A1* | 12/2011 | Winquist et al. | 506/9 |

FOREIGN PATENT DOCUMENTS

| | | |
|---|---|---|
| JP | 11-326323 A | 11/1999 |
| JP | 2002-537563 A | 11/2002 |
| JP | 2003-57555 A | 2/2003 |
| JP | 2005-513497 A | 5/2005 |
| JP | 2009-204408 A | 9/2009 |
| JP | 2009-270990 A | 11/2009 |

* cited by examiner

FIG. 3
(A)
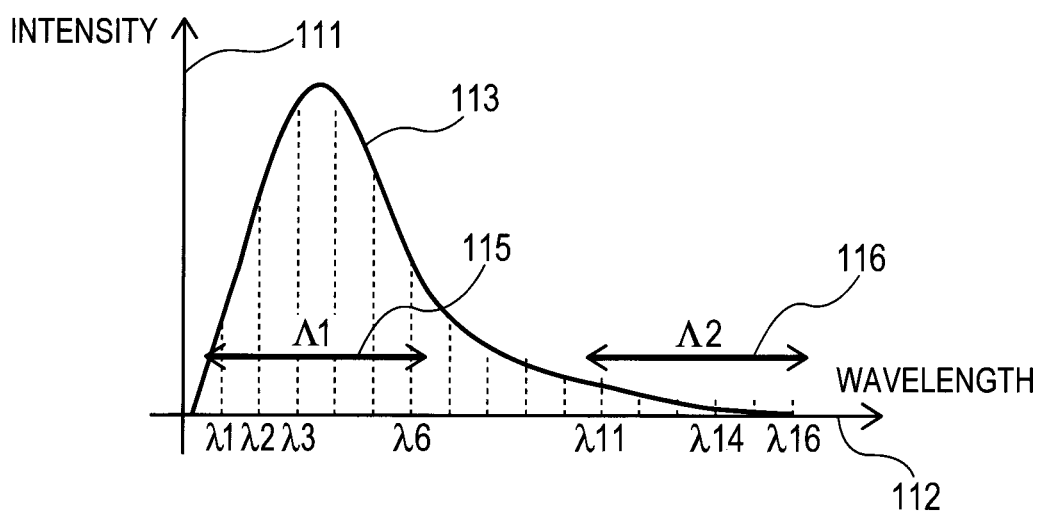
(B)
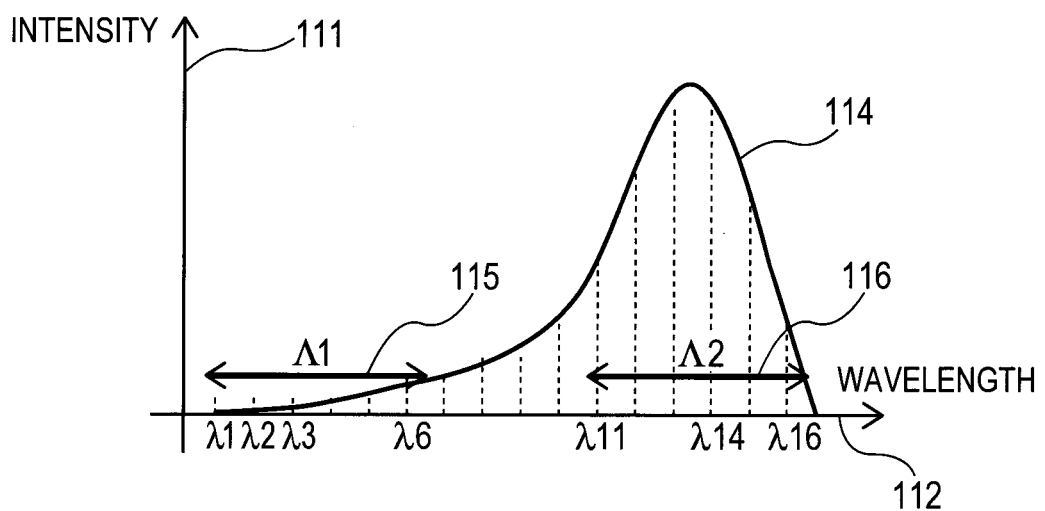

FIG. 4
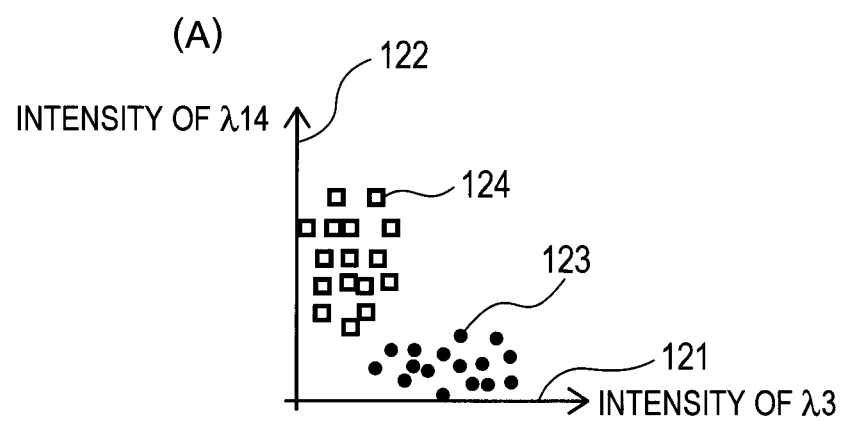
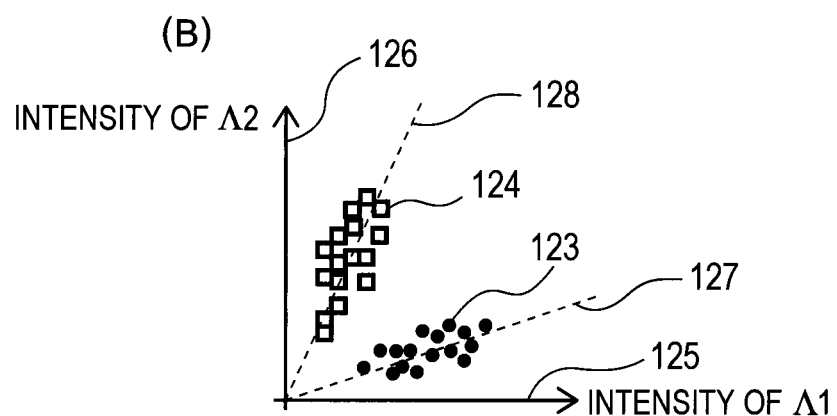

FIG. 14

|  | SAMPLE 1 | SAMPLE 2 | SAMPLE 3 | ... | SAMPLE n |
|---|---|---|---|---|---|
| SAMPLE 1 | – | 0.03 | 0.02 | ... | 0.001 |
| SAMPLE 2 | 0.03 | – | 0.01 | ... | 0.005 |
| SAMPLE 3 | 0.02 | 0.01 | – | ... | 0.008 |
| : | : | : | : |  | : |
| SAMPLE n | 0.001 | 0.005 | 0.008 | ... | – |
| REJECT RATE | 0.01 | 0.03 | 0.02 | ... | 0.08 |

FIG. 19

|  | SAMPLE 1 | SAMPLE 2 | SAMPLE 3 | ... | SAMPLE n |
|---|---|---|---|---|---|
| SAMPLE 1 | 5±3 | 0.01±0.1 | 0.02±0.05 | ... | 0.001±0.5 |
| SAMPLE 2 | 0.03±0.01 | 3±2 | 0.01±0.3 | ... | 0.005±0.3 |
| SAMPLE 3 | 0.02±0.2 | 0.01±0.05 | 7±1 | ... | 0.008±0.2 |
| : | : | : | : |  | : |
| SAMPLE n | 0.001±0.1 | 0.005±0.2 | 0.008±0.3 | ... | 6±0.5 |
| REJECT RATE | 0.01 | 0.03 | 0.02 | ... | 0.08 |

FIG. 20
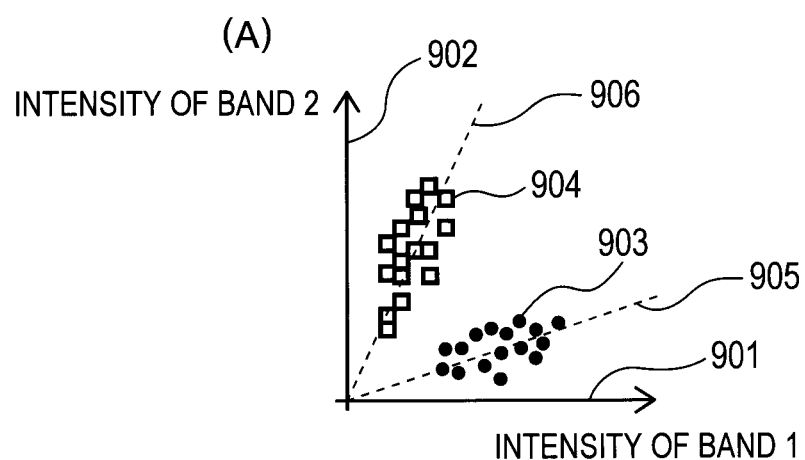
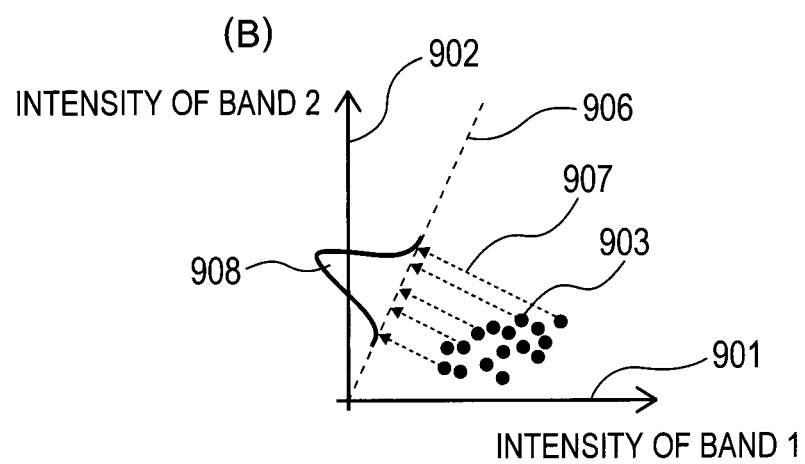

ANALYTICAL APPARATUS AND ANALYTICAL METHOD

TECHNICAL FIELD

The present invention relates to a flow type particle analysis method and the same apparatus to perform quantitative analysis of particles (including cells) in a flow cell, in particular, pertaining to a flow type particle analysis method and the same apparatus provided with a post-spectral device and a multi-channel optical detection unit.

BACKGROUND ART

As one of the apparatuses to quantitatively analyze particles in a flow cell, a flow cytometer is known, which is arranged such that a fluorescence-labeled sample (cells and particles) is fed into a flow and a laser beam is irradiated onto the flow so that the intensities of scattering light and fluorescence emitted from the sample are measured and the natures of such sample are quantified from such intensities. The fluorescence labeling of the sample, in which specific objects of the cellular surface and interior are labeled, is performed for quantifying the targeted objects and determining the kinds of the cells. Normally, such fluorescence labeling is carried out not only with simple stain, but also with multiple stain. The structural arrangement of one of the conventional apparatus for detecting such multiple stain is shown in FIG. 15. The fluorescence-stained sample 610 forms a flow of such sample within the flow cell 630 with the sample interposed between a sheath solution 620, in which flow the cells (particles) are one by one aligned in one row. The sample 610 is excited with a laser beam 650 so that scattering light and fluorescent light are generated. The fluorescent light is split by a dichroic mirror 660 so as to be selectively detected as its respective kinds through band pass filters 670 matching such respective kinds. A PMT (Photo-Multiplier Tube) 680 and so forth is adopted for a detector. After the detected light components are converted into electric signals (voltage pulses) at the electric signal processing section 640, such signals are numerically expressed so as to be subjected to statistic analysis such as histogram by the software 690 exclusive for such analysis. However, when it is wished that the number of fluorescent color lights to be analyzed by such conventional apparatus be incremented, it requires that filter-sets and detectors be incremented thereto, so that such problems happen as the apparatus as a whole becoming large in size and expensive to manufacture and the abatement of fluorescence intensity caused by the dichroic mirror becoming remarkable. Further, when it is wished that a fluorescent color to be analyzed be changed without increasing such color lights, disadvantageously, it requires that a filter-set matching such color change be purchased.

In recent years, the cell function analysis employing fluorochromes capable of measuring an ion concentration of calcium and so forth in a cell prevails over the related field. It is known that as with those fluorochromes, the central wavelength of fluorescence is shifted due to the cellular conditions, the level of pH and temperature thereof, for examples. However, with the above-mentioned apparatus, a fluorescent wavelength band detectable by the same is restricted according to the filter in use and results in being intermittently detected, so that disadvantageously it turns out to be hard to detect the shifting of the central wavelength (peak wavelength) of fluorescence.

The rearrangements of such apparatus are disclosed in Patent Documents 1 and 2. In Patent Document 1, there is disclosure on a microtiter plate reader while in Patent Document 2, there is disclosure on a laser microscope, any of which uses a spectral device such as a diffraction grating and prisms on behalf of the conventional filter-set and a multi detector such as multi PMTS in series and CCDs on behalf of the individual PMTS. Such rearrangement does without purchasing a new filter-set and exchanging the same as well as restrains the fluorescence intensity owing to such filter-set from being abated. Further, when multiple stain measurement is carried out, a wavelength band to be detected can be set in such a band as being invulnerable to crossover of fluorescence. Moreover, since a detection width can be set in a readily manner, the sensitivity also can be freely modified.

CITATION LIST

Patent Literature

Patent Literature 1: International Application Republication in Japanese No. 2005-513497
Patent Literature 2: Japanese Patent Unexamined Application Publication No. 2003-057555

SUMMARY OF INVENTION

Technical Problem

FIG. 16 exemplarily shows the relationship between the fluorescence spectra of three types of fluorochromes and a wavelength band to be detected. The vertical axis 700 indicates a fluorescence intensity while the horizontal axis 705 indicates a wavelength. The curved lines 710, 720 and 730 indicate the spectra of such three types of fluorochromes 1, 2 and 3. In this example, the spectrum 730 of the fluorochrome 3 has a small peak at the region 740 circled with an oval. According to the conventional apparatus, it is defined that three band-like regions shown in the numeral reference 750 are wavelength bands to be detected due to the characteristics of the band pass filter. In this case, a band to be detected of the shortest wavelength region encompasses the peak of the spectrum 710, the small peak of the spectrum 730 and the left foot portion of the peak of the spectrum 720, so that self-evidently a signal can be detected for the respective fluorescent lights of those three types of fluorochromes. That is to say, the sharpness of separation of such lights is deteriorated.

On the other hand, when a spectroscope and a multi detector are employed, an arbitrary band can be set with wavelength bands 770 covered by one detector rendered into a unit. For example, the setting of a wavelength band like the three band-like regions shown with the reference numeral 760 is feasible. This allows the band of the shortest wavelength side to be set such that such band encompasses only the peak of the spectrum 710, so that it permits the fluorescent lights of the respective fluorochromes to be separated with a higher precision than the related art.

However, when the apparatus is arranged such that it is provided with a spectral device such as a diffraction grating and a multi detector, as shown in FIG. 16, it requires that a wavelength band in which a target fluorescent light is detected be preliminarily established before a sample is measured.

In Patent Document 1, there is disclosure that a fluorescent spectrum imaging is gained with a standard sample labeled with the same fluorescence as a sample in use; and the user selects a wavelength band less affected by the overlapping of fluorescent lights. However, there is no method disclosed therein upon an actual sample being measured to evaluate how high the precision of separating the target fluorescence intensity from the out-of-target one is. Thus, there is possibility that in the case where such spectral device and multi detector are adopted for a flow cytometer, the user might repeat the setting of a wavelength band while an actual sample is being measured so that it takes a lot of labor during such measurement.

In Patent Literature 2, there is disclosure that a wavelength band is not established in the first place, but the user selects an optimum wavelength band after having gained an image with a laser microscope. This method cannot be applied to a flow cytometer that requires the fluorescence intensity measurement of a sample in a real-time manner.

Namely, with a flow cytometer employing a spectral device and a multi detector, the issue is how an optimum wavelength band is established before the fluorescence intensity measurement is carried out in a real-time manner.

Solution to Problem

In order to solve the above problem, the present analytical system is characterized in comprising a light source; a flow cell to flow a sample receiving light from the light source and emitting light; a spectral device to diffract the light emitted from the sample; a detection section provided with a plurality of detectors to detect the diffracted light outputted from the spectral device per different wavelength; a signal processing unit to process a signal of the light detected by the detection section; an input unit to receive an instruction input for the signal processing; a storage section to store a result of the processed signal; an output section to display the result; and a band-setting unit to set a wavelength band to be detected by at least one of the detectors through the input unit, in which the storage section stores the signal of the detected light on a plurality of the samples different from each other in the respective detectors and an intensity of the signal of the detected light at the respective detectors for the respective samples is displayed on the output section.

Then, the analytical method makes use of a light source; a flow cell to flow a sample; a spectral device to diffract light emitted from the sample receiving light from the light source and flowing through the flow cell; a plurality of detectors to detect the diffracted light outputted from the spectral device per different wavelength; a processing unit to process a signal of the light detected by the detectors; a storage unit to store data; an input unit to do an input to the processing unit; and an output section to output the processed result. The storage section stores the signals of the light detected on a plurality of the samples different from each other flowed through the flow cell for the respective detectors, which method comprises the steps of: displaying an intensity of the signal of the detected light at the respective detectors for the respective samples; setting a wavelength band to be detected by at least one of the detectors through the input unit; storing the set wavelength band in the storage section; detecting light from an analyte flowing through the flow cell with the detectors; and outputting a signal of the analyte to the output section with the set wavelength band in use.

Advantageous Effects of Invention

Calculating a spectrum of a calibration sample and displaying the same allows an optimum band to be set with intrinsic fluorescence and a peak shift taken into account upon such band being set at the measurement.

BRIEF DESCRIPTION OF DRAWINGS

FIG. 3 shows examples of the spectra of fluorochromes.

FIG. 4 shows the distribution of the signal intensities upon the fluorochromes emitting light.

FIG. 14 is a view showing an example for displaying the information on the estimated measurement accuracy.

FIG. 19 is a view showing an example for displaying the estimated measurement accuracy information.

FIG. 20 is a view to explain how to calculate components of projection of a calibration sample band intensity distribution to the principal axis of the other calibration sample band intensity distribution.

DESCRIPTION OF EMBODIMENTS

First Embodiment

The following explains the present embodiment in which a spectral device and a multi detector are applied to a flow cytometer with reference to the accompanying drawings.

Figure 1:
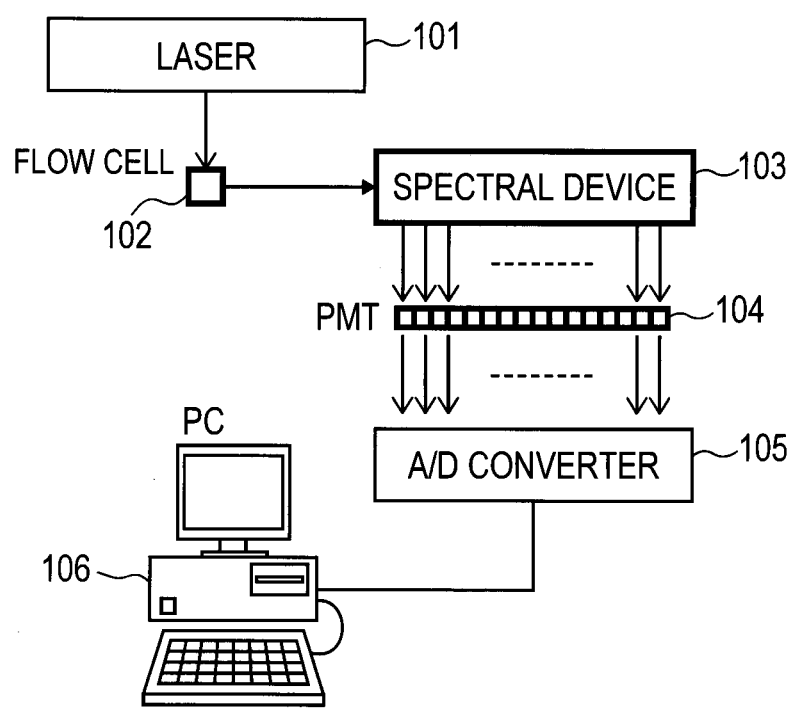
FIG. 1 is a view showing the schematic view of a flow cytometer.

FIG. 1 is a schematic view of the flow cytometer. The solution (hereinafter, referred to as 'analyte') containing target particles preliminarily subjected to fluorescent label to be measured passes at a constant speed through a flow cell 102 from the top surface to the backside of the sheet in which FIG. 1 is depicted. A laser beam emitted from a laser 101 is irradiated onto the flow cell 102. Upon the target particles passing through the flow cell 102, fluorochromes are excited by the laser beam so as to emit light. The emitted light is diffracted into a plurality of wavelength components with a spectral device 103 and the diffracted light is converted into electric signals with a plurality of PMTs. The electric signals outputted from the PMTS 104 are converted into digitalized signals with an A/D converter 105 so as to be inputted into a signal processing unit 106. At the signal processing unit 106, based on the fluorescent intensities measured for the respective wavelengths, the classification of the particles and the analysis on their components and natures are carried out.

The spectral device 103 may be formed of a condensing lens and a diffraction grating. Prisms may well be used instead of the diffraction grating. Further, it may well be formed of a plurality of optical filters and a dichroic mirror.

A PC provided with a keyboard, a mouse and a display may be adopted for the signal processing unit. However, when the processing speed is enhanced, a high-speed computation board may well be disposed in the PC or between the PC and the A/D converter 105. Further, such unit may well be realized not as a PC, but as a hardware exclusive for such processing. Hereupon, it is exemplified herein that the outputting unit is in the form of a display on the screen of PC while the inputting unit is in the form of an instruction input into such display on the screen through a mouse and a keyboard, to which such unit are not limited, but may be in any form to enable such input and output to be feasible.

Figure 2:
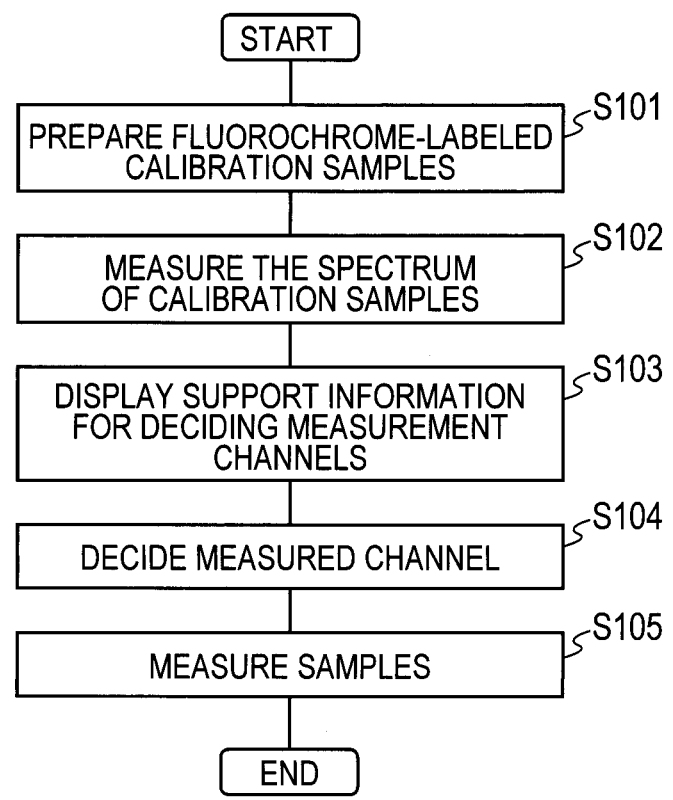
FIG. 2 is a flow chart showing the measuring procedures with a flow cytometer.

Then, the following explains the processing flow upon measuring an analyte using a flow cytometer shown in FIG. 1 with reference to FIG. 2. It is noted herein that a plurality of fluorochromes are used for measurement, and the analysis of the particles is made through fluorescent lights emitted by such particles.

The user who makes a measurement in the first place prepares calibration samples before the analyte is measured (Step S101). Those samples are respectively labeled with one of the plural fluorochromes used for such measurement. For instance, when three kinds of fluorochromes: A, B and C are used, three corresponding samples or a sample labeled with A, a sample labeled with B and a sample labeled with C are prepared. As the calibration sample, a preliminarily labeled minute bead or a part of the analyte to be measured may well be used.

Then, the fluorescence spectrum of the calibration sample is measured (Step S102). More concretely, the calibration sample is flowed through a flow cytometer as shown in FIG. 1, and the fluorescence intensity of the respective particles in such sample is converted into an electric signal with the respective PMTs as shown in FIG. 1 and an output value outputted from the A/D converter is stored for the respective measurement channels. The outputted value is stored in the storage device within the signal processing device (PC) 106. Herein, it is exemplified herein that there are 16 PMTs in total. In this case, 16 pieces of data are obtained for the respective particles, and those pieces are stored by as many particles as detected. The above measurement is repeated by as many times as the number of kinds of the calibration samples or that of kinds of fluorochromes in use.

Hereupon, in order to simplify the explanation, it is exemplified herein that there are 16 PMTs in total as mentioned above and the wavelengths to be measured by the respective PMTs are $\lambda 1$ to $\lambda 16$ while two kinds of flurochromes A and B are used. Further, it is exemplified herein that the fluorochromes have the spectra as shown in FIG. 3.

In FIG. 3, (A) shows the fluorescence spectrum of the fluorochrome A while (B) shows that of the fluorochrome B. The vertical axis 111 indicates a fluorescence intensity while the transversal axis 112 indicates a wavelength. The curved lines 113 and 114 indicate the spectra of the fluorochromes A and B. Further, $\lambda 1$ to $\lambda 16$ shown on the transversal axis indicate wavelengths measured by those 16 PMTs.

Measurement is carried out after those two fluorochromes are added to the analyte to be measured. How far the respective fluorochromes A and B are connected to the particles is estimated by measuring fluorescent lights emitted by the particles in the analyte, based on which the natures of the particles are determined. When the flurochromes A and B have fluorescence spectra shown in FIGS. 3 (A) and (B), the fluorescence intensity of the fluorochrome A is very strong while that of the fluorochrome B is very weak at the wavelength $\lambda 3$. On the contrary, that of the fluorochrome B is very strong while that of the fluorochrome A is very weak at the wavelength $\lambda 14$. Hereupon, when those wavelengths $\lambda 3$ and $\lambda 14$ are used for measuring the analyte, the intensity at the wavelength $\lambda 3$ included in the light emitting intensity of the particles indicates an amount of the fluorochrome A while that at the wavelength $\lambda 14$ included therein indicates an amount of the fluorochrome B. That is to say, measuring the intensities of the wavelengths $\lambda 3$ and $\lambda 14$ allows the amount of materials labeled with the fluorochrome A included in the respective particles and that of those labeled with the fluorochrome B to be estimated.

However, when the apparatus with the arrangement illustrated in FIG. 1 is used, the wavelength band of light incident to the respective PMTS is so narrow that amount of light incident to each PMT is too a little, with the result that a signal of the respective PMTS is very small so as to be interfered with noises. Ideally speaking, upon the fluorochrome A emitting light, only the intensity at the wavelength $\lambda 3$ appears while that at the wavelength $\lambda 14$ is 0. On the contrary, upon the fluorochrome B emitting light, the wavelength $\lambda 3$ is 0 while only that at the wavelength $\lambda 14$ appears. However, noises occur owing to the above reason, so that when only the fluorochrome A emits light, the intensity at the wavelength $\lambda 14$ appears while when only the fluorochrome B emits light, the intensity at the wavelength $\lambda 3$ appears, which situation is exemplarily shown in FIG. 4(A) along with the distribution of the signal intensities. The transversal axis 121 shows the intensity of the wavelength $\lambda 3$ while the vertical axis 122 shows that of the wavelength $\lambda 14$. Further, the numerical reference 123 shows the distributions of the signal intensities of $\lambda 3$ and $\lambda 14$ measured upon the fluorochrome A emitting light while that 124 shows those measured upon the fluorochrome B emitting light. In FIG. 4, one numerical reference (point) indicates the fluorescence intensity of one particle included in the sample.

In an idealistic case where there is no noise in the signals, the signal intensities measured upon the fluorochrome A emitting light are distributed over the transversal axis while those measured upon the fluorochrome B emitting light are distributed along the vertical axis. In this case, it is defined that the intensity at the wavelength $\lambda 3$ is the light emitting intensity of the fluorochrome A while that at the wavelength $\lambda 14$ is that of the fluorochrome B. However, where there are a number of noises, as shown in FIG. 4 (A), the distribution of the signal intensities upon the fluorochrome A emitting light extends in the direction of the vertical axis while that upon the fluorochrome B emitting light extends in the direction of the transversal axis. That is to say, providing that the intensity at the wavelength $\lambda 3$ is the light emitting intensity of the fluorochrome A and that at the wavelength $\lambda 14$ is that of the fluorochrome B, such an error occurs as if the fluorochrome B also dimly emitted light in spite of the fact that only the fluorochrome A emits light.

In order to minimize such error, it requires that the extent to which the distribution of the signal intensities measured upon only the fluorochrome A emitting light extends in the vertical direction and that to which the distribution of the intensities measured upon only the fluorochrome B emitting light extends in the transversal direction be rendered as small as possible. In order to mitigate influences caused by the noises and make such extents as small as possible, the signals of the plural PMTS may well be added.

For example, in FIG. 3, it is defined herein that the band from $\lambda 1$ to $\lambda 6$ is $\Lambda 1$ and the intensity of $\Lambda 1$ is calculated by adding intensities of wavelengths within such band while the band from $\lambda 11$ to $\lambda 16$ is $\Lambda 2$ and the intensity of $\Lambda 2$ is calculated by adding intensities of wavelengths within such band. Since the $\Lambda 1$ and $\Lambda 2$ result from the addition of plural signals, random noises are set off so that the noises are relatively mitigated. However, the fluorescence spectrum of the fluorochrome A as shown in FIG. 3 (A) has a slight intensity in the vicinity of $\lambda 11$, so that the intensity of the $\Lambda 2$ is also slightly measured upon only the fluorochrome A emitting light. On the other hand, the fluorescence spectrum of the fluorochrome B as shown in FIG. 3 (B) has a slight intensity in the vicinity of $\lambda 6$, so that the intensity of the $\Lambda 1$ also is slightly measured upon only the fluorochrome B emitting light.

The distribution of the signal intensities according to the above situation is exemplarily shown in FIG. 4 (B), in which the transversal axis 125 and the vertical axis 126 indicate the intensity of $\Lambda 1$ and that of $\Lambda 2$ respectively. The distribution 123 of the signal intensities upon only the fluorochrome A emitting light is such that the intensity of $\Lambda 1$ is large while that of $\Lambda 2$ is small, with the result that such distribution extends in the direction of a broken line 127. The distribution 124 of the signal intensities upon only the fluorochrome B emitting light is such that the intensity of $\Lambda 1$ is small while that of $\Lambda 2$ is large, with the result that such distribution extends in the direction of a broken line 128. Hereupon, a length of the measured signal intensities projected onto the broken line 127 can be considered as the light emitting intensity of the fluorochrome A while that projected onto the broken line 128 can be considered as that of the fluorochrome B. The $\Lambda 1$ and $\Lambda 2$ result from the addition of the signal intensities of plural wavelengths, so that the noise components are reduced, with the result that the extent to which the distribution 123 of the signal intensities upon only the fluorochrome A emitting light straightly extends in the orthogonal direction of the broken line 127 becomes smaller than that to which the distribution of such intensities extends in the direction of the vertical axis as shown in FIG. 4 (A). Further, the extent to which the distribution 124 of the signal intensities upon only the fluorochrome B straightly extends in the orthogonal direction of the broken line 128 becomes smaller than that to which the distribution of such intensities extends in the direction of the transversal direction as shown in FIG. 4 (A). However, a center-to-center distance between those distributions 123 and 124 becomes shorter than that shown in FIG. 4 (A).

In view of the foregoing, making wavelength bands used for the measurement selectively narrower leads to enlarging the extents to which the light emitting intensities of the fluorochromes A and B are distributed so as to amplify such error. Further, making such band selectively wider leads to reducing such extents while the center-to-center distance between such two distributions becomes shorter so as to vulnerably invite such error. With the flow cytometer as shown in FIG. 1, as mentioned above, how wavelength bands (channels of PMTS) are selected largely affects precision in the measurement. Thus, at Step S103 of FIG. 2, it is arranged herein that information to support a user to select channels is displayed upon such user determining the channels used for the measurement.

At Step 104 of FIG. 2, the channels that the user uses for the measurement are determined and at Step 105 thereof, the measurement of the actual analyte is performed.

Figure 5:
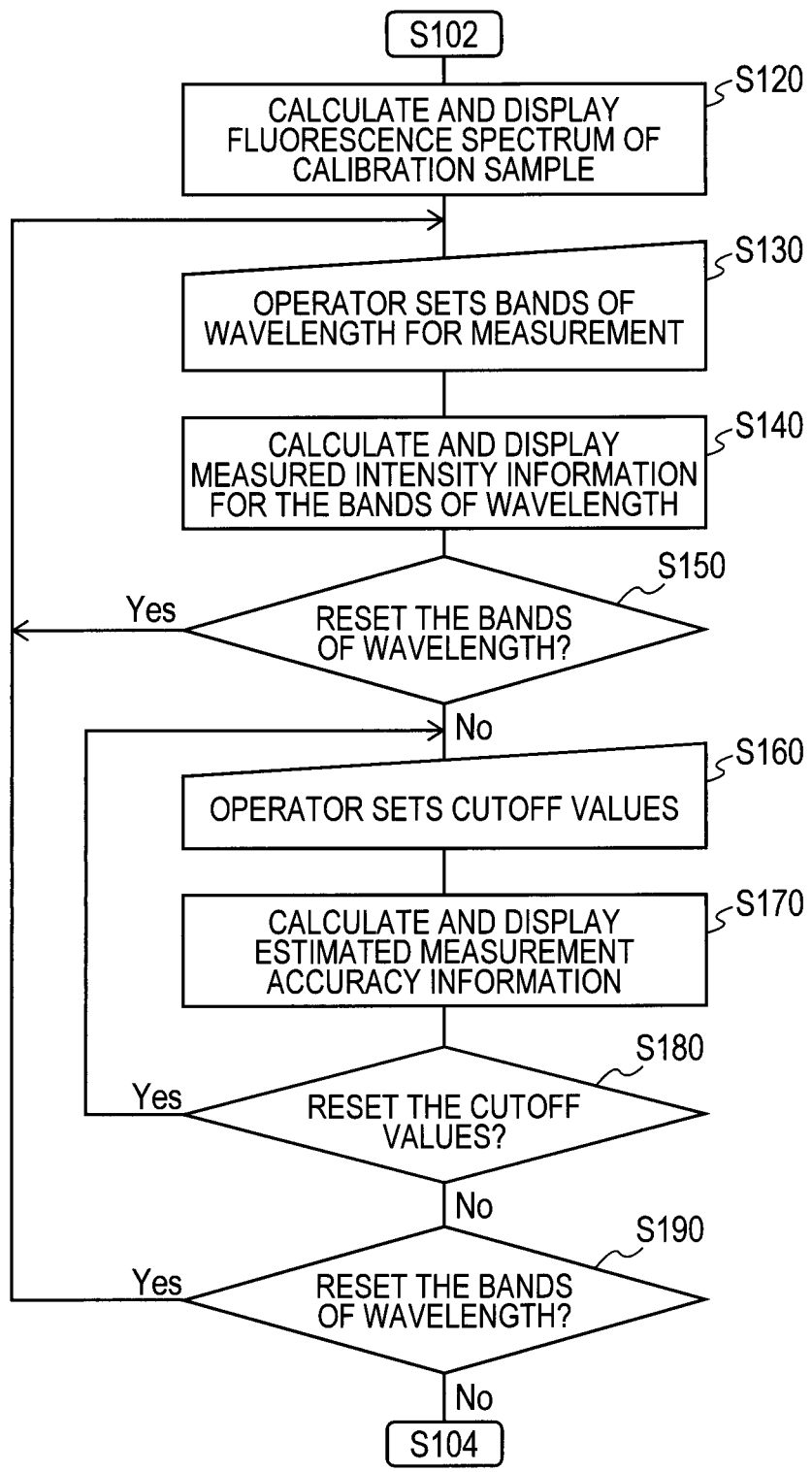
FIG. 5 is a view showing the detailed processing flow for displaying support information for deciding measurement channels.
Figure 6:
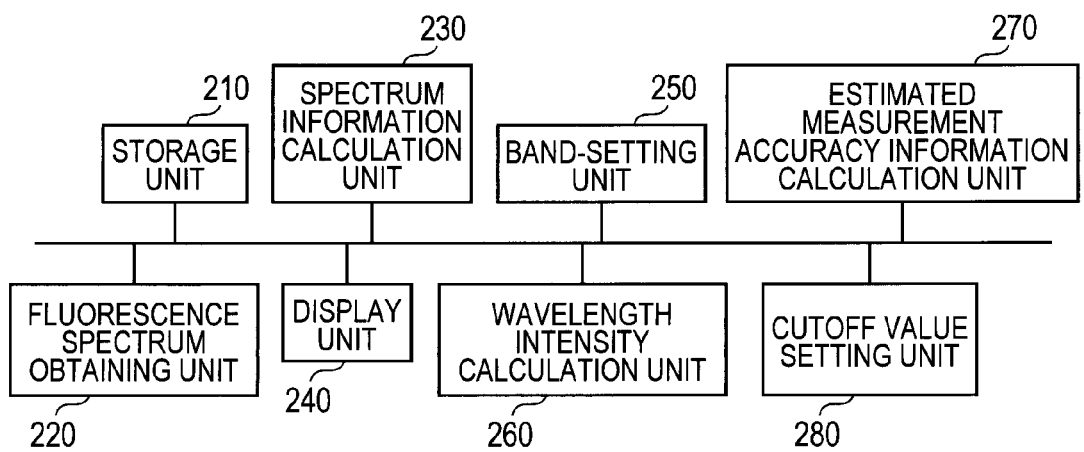
FIG. 6 is a view showing the structural arrangement of the apparatus to perform displaying support information for deciding measurement channels.

Then, an example of the detailed processing for displaying support information for the user to decide measurement channels at Step 103 thereof is in detail explained with reference to FIGS. 5 and 6. FIG. 5 shows the further detailed processing flow of Step 103 while FIG. 6 shows the arrangement of the apparatus to perform the processing shown in FIG. 5. To note, the processing shown in FIG. 6 is executed by the signal processing unit 106 shown in FIG. 1, and the arrangement shown in FIG. 5 may well be implemented as a hardware exclusive for that purpose in the signal processing unit or be implemented as a processing block of the software. To note, at Step 102 thereof, it is arranged herein that the fluorescence spectra emitted by the particles in the calibration sample are measured by the fluorescence spectrum obtaining unit 220 and the measured spectra are stored in the storing unit 210.

Figure 7:
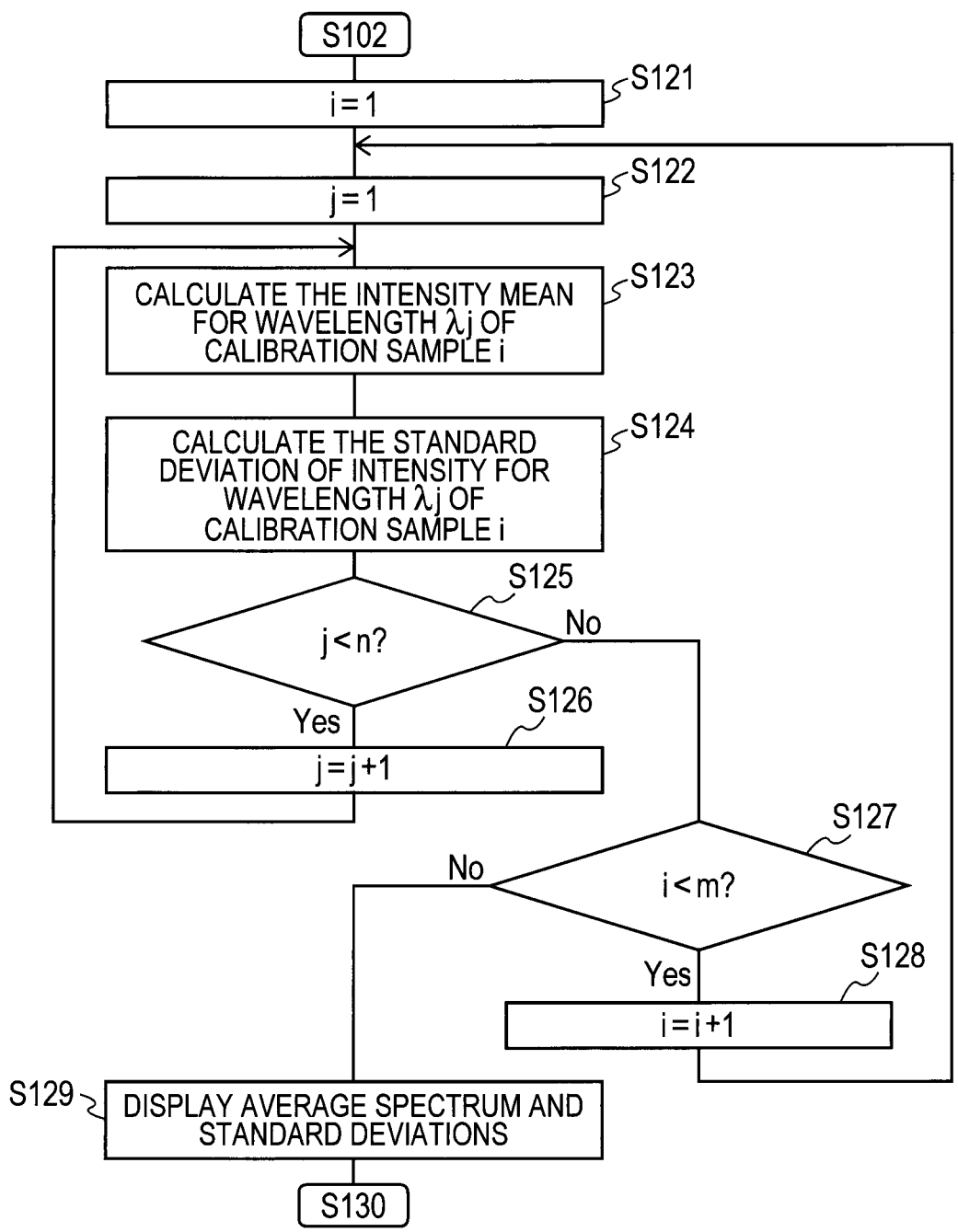
FIG. 7 is a view showing the detailed processing flow for calculating and displaying a fluorescence spectrum of a calibration sample.

In the first place, at Step S120 of FIG. 5, the spectrum information calculation unit 230 calculates the fluorescence spectra emitted by the particles in the calibration sample and the calculated spectra are displayed on the display unit 240. The processing performed at Step S120 is in detail explained with reference to FIG. 7. Hereupon, it is defined that the kinds of the calibration sample are 'm'; the number of channels of PMTs is 'n'; and a wavelength of light measured by the 'j'-th positional channel is $\lambda j$. To the beginning, at Step S121, '1' is assigned to a variable 'i' indicating the kind of the calibration sample for initialization. At the subsequent Step S122, '1' is assigned to a variable 'j' indicating channels of PMTs for initialization.

At the subsequent Step S123, among lights emitted by the particles in the calibration sample, the signal intensities at the wavelength $\lambda j$ of the respective particles measured by the 'j' th channel of the PMTs are retrieved from the storing unit 210 and their mean value '$\mu ij$' is calculated. Likewise, at Step S124, the standard deviation '$\sigma ij$' of the wavelength $\lambda j$ of the respective particles is calculated. At Step S125, comparing the variable 'j' with the 'n', whether or not the mean value and the standard deviation have been calculated as to the whole wavelengths of the calibration sample 'i' is determined. When such calculations are over as to the whole wavelengths (j=n), it proceeds to Step S127. When there are left undone some wavelengths (j<n), '1' is added to 'j' at Step S126 and the steps starting from S123 inclusive are performed for the following wavelength. Hereupon, it is exemplified that the mean value and the standard deviation are calculated for the whole wavelengths, but necessary information may well be picked up according to an object to which the present analytical processing is performed.

At Step S127, comparing 'i' with 'm', whether or not calculation has been performed for the whole calibration sample is determined. When the calculation is over for the whole samples (i=m), it proceeds to Step 129. When there are left undone some samples (i<m), '1' is added to 'i' as Step S128, and the steps starting from S122 inclusive are performed for the following calibration sample.

Figure 8:
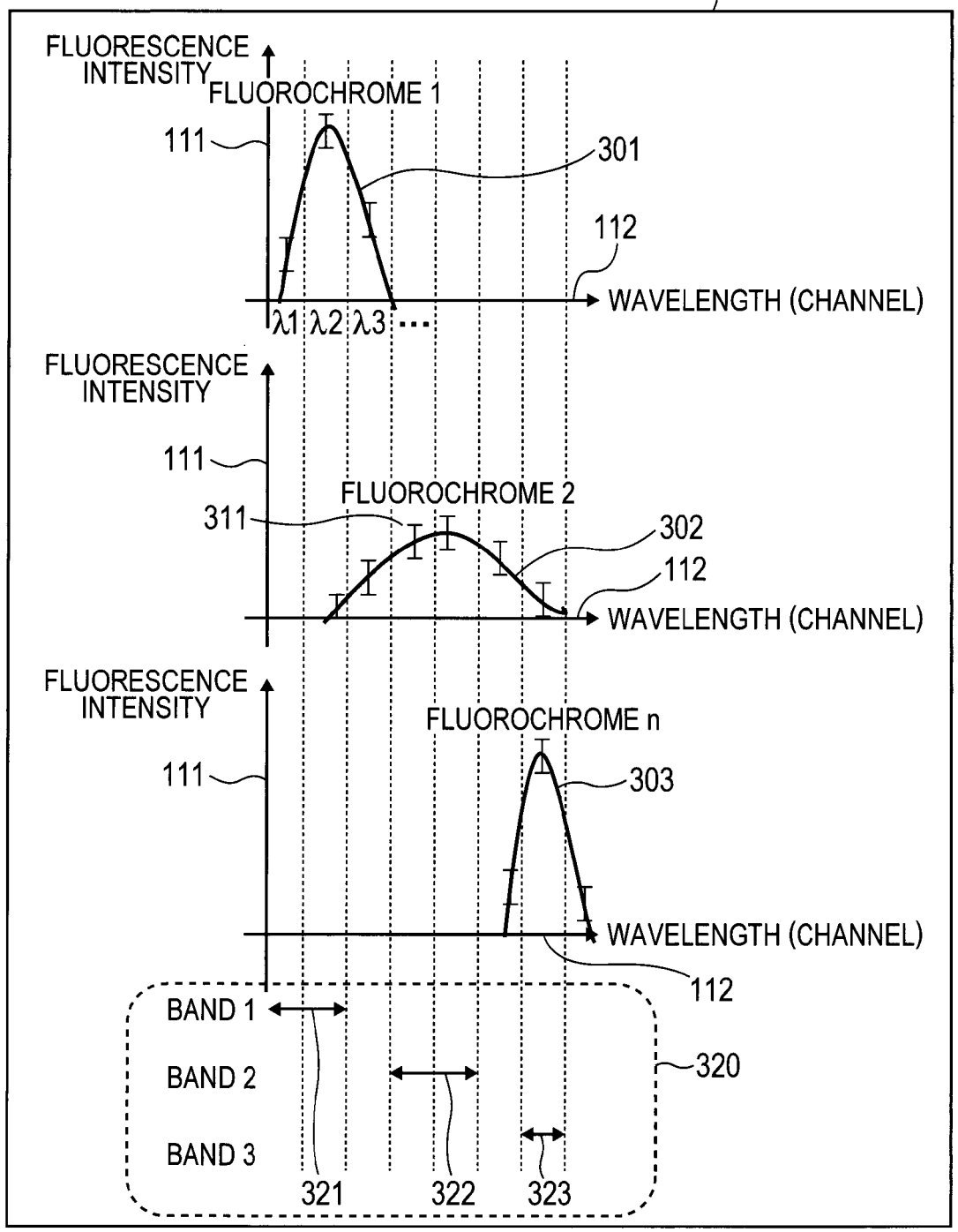
FIG. 8 is a view showing an example of a fluorescence spectrum display screen of a calibration sample.

At Step S129, the calculated mean value '$\mu ij$' and the standard deviation '$\sigma ij$' of the signal intensity of the respective wavelengths (respective channels of PMTs) are stored in the storing unit 210 so as to be displayed on the display unit 240 as an average fluorescence spectrum. A screen example in which the same is displayed on the display unit 240 is shown in FIG. 8.

The average fluorescence spectrum is displayed in its display area 300 on the screen of the display unit 240. In FIG. 8, it is exemplified that there are three kinds of the calibration samples, so that spectra of such three kinds are displayed. The vertical axis 111 indicates a fluorescence intensity while the transversal axis 112 indicates a wavelength. The curved lines 301, 302 and 303 are such that the mean values ($\mu 1j$, $\mu 2j$, $\mu 3j$, in which j=1 to n) of the signal intensities at the respective wavelengths of the samples 1, 2 and 3 are plotted so as to indicate an average fluorescence spectrum of the respective samples. Further, a vertical bar 311 displayed on the average fluorescence spectrum indicates the standard deviation of the signal intensities at the corresponding wavelength.

Each fluorochrome in use has a spectrum inherent in itself. When they are added to the samples for the measurement, there are some cases where unexpected fluorescent light other than such fluorochromes in use such as intrinsic fluorescence and a peak shift might occur, which leads to showing spectral shapes different from those inherent in the fluorochromes in use. As described above, calculating the average fluorescence spectrum and displaying the same allows spectral shapes as measured different from those inherent in fluorochromes in use to be preliminarily confirmed so as to permit by far an optimum wavelength band to be set for more accurate measurement.

Further, the spectra inherent in fluorochromes in use are observed for the whole stained particles in the sample, so that fluctuation of spectra at each wavelength results in reflecting that of the intensities thereat, so that substantially the same fluctuation occurs over the whole wavelengths. On the other hand, as for intrinsic fluorescence and a peak shift, they occur only in some particles (cells) in the sample, so that it is considered that the fluctuation in the distribution of the intensities at a wavelength affected by them is further intensified. Thus, calculating the standard deviations of the intensities at the respective wavelengths of the average fluorescence spectra and displaying the same facilitates at which wavelength such intrinsic fluorescence and peak shift occur to be estimated so as to permit by far an optimum wavelength band to be set for more accurate measurement.

Then, at Step S130 of FIG. 5, the user sets wavelength bands to be measured. The user sets a width of such band with the band-setting area 320 provided below the average fluorescence spectrum display area 300 as shown in FIG. 8 in use. In this illustration, it is exemplified that three kinds of bands (1, 2 and 3) are set. The user sets such band by clicking both ends of the corresponding band with a mouse or by dragging or dropping the mouse from one end of such band to the other end thereof. The arrows 321, 322 and 333 shown in FIG. 8 exemplify wavelength bands set for those bands 1, 2, and 3 therein. To note, controlling of the screen of the band setting area 320 and importing of information on the bands set by the user are performed by the band-setting unit 250. Further, the bands set by the user are stored in the storing unit 210.

Figure 9:
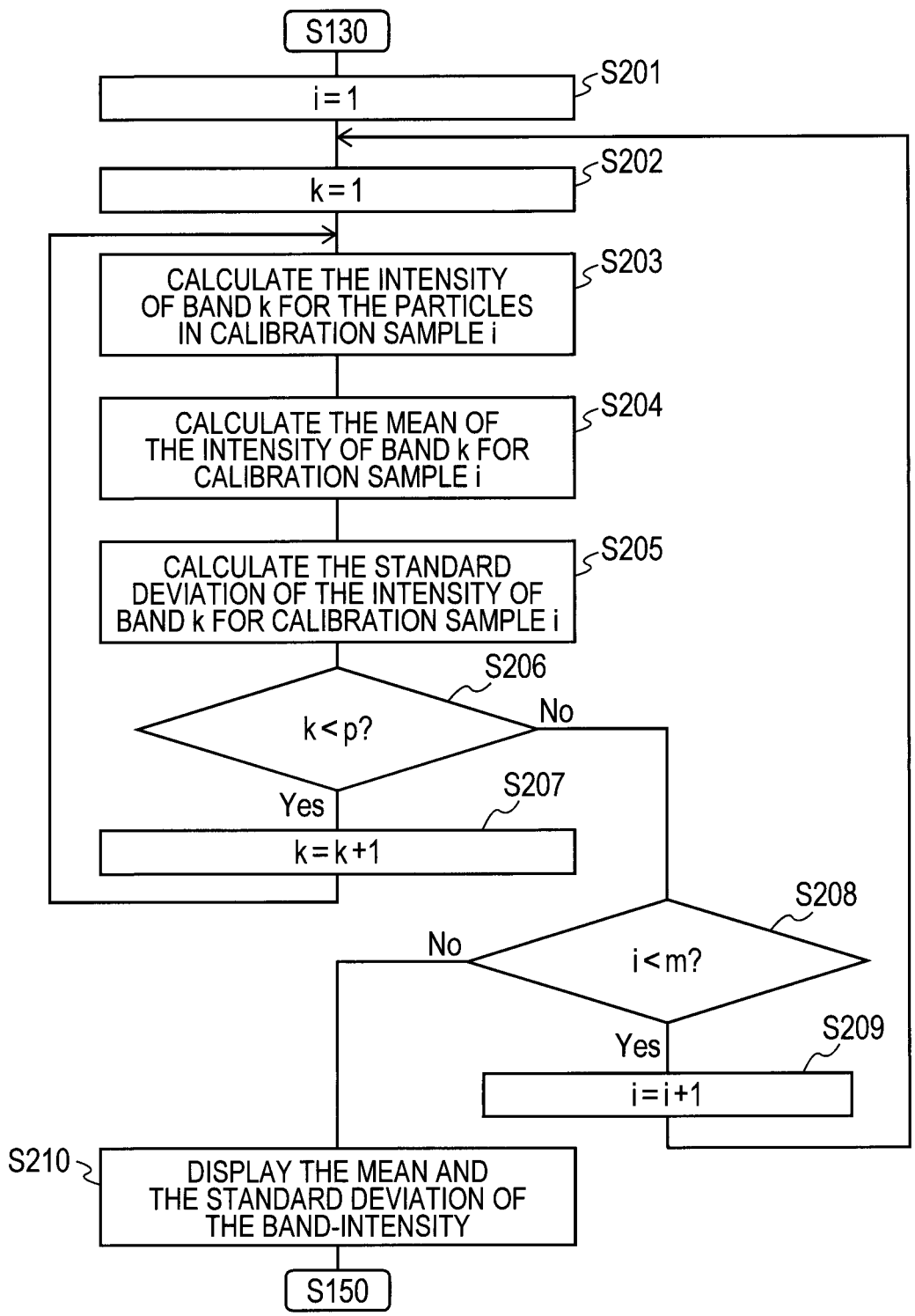
FIG. 9 is a view showing the detailed processing flow for calculating and displaying information on a measured wavelength band intensity.

Then, at Step S140 of FIG. 5, the wavelength intensity calculation unit 260 calculates the signal intensities at the respective bands set at Step S130 with reference to fluorescent lights of the particles in the calibration sample and computes the mean values and the standard deviations of the signal intensities at the respective bands, which results are stored in the storing unit 210 and displayed on the display unit 240. The processing performed at Step S140 is in detail explained with reference to FIG. 9. Hereupon, it is exemplified that the kinds of the calibration sample are 'm' and the number of the bands set by the user is 'p'. At first, at Step S201, '1' is assigned to a variable 'i' indicating the kinds of the calibration sample for initialization. At the subsequent step S202, '1' is assigned to a variable 'k' indicating a band number for initialization.

Then, at Step S203, the signal intensities in the wavelength band 'k' set by the user for the respective particles in the calibration sample 'i' are calculated with reference to the signals measured by the respective channels of PMTS. More concretely, it is defined herein that the total sum of the signal intensities of the wavelengths (channels of PMTS) included in the band 1 is the signal intensity of that band. For instance, it is supposed that the band 1 includes the wavelengths $\lambda 1$, $\lambda 2$ and $\lambda 3$ and the intensities of a certain particle at the wavelengths $\lambda 1$, $\lambda 2$ and $\lambda 3$ are r1, r2 and r3. Providing that the intensity of that particle in the band 1 is R1, the signal intensity of that band is calculated according to the following equation: R1=r1+r2+r3. The calculated signal intensities of the respective particles in the band 'k' are stored in the storing unit 210.

With the signal intensities in the band 'k' calculated at Step S203 in use, the mean value 'Mik' of such intensities is computed at Step S204. Likewise, at Step S205, the standard deviation 'Sik' of such intensities is calculated. At Step S206, comparing the variable 'k' with the number of bands 'p', whether or not the mean values and the standard deviations for the whole bands of the calibration sample 'i' have been calculated is determined. When such calculations are finished for the whole bands (k=p), it proceeds to Step S208. When there are left undone some bands (k<p), '1' is added to the 'k' at Step S207 and the steps starting from S203 inclusive are performed for the following band.

At Step S208, comparing the variable 'i' with the kinds of the sample 'm', whether or not such calculations have been performed for the whole calibration samples is determined. When such calculations are finished for the whole samples (i=m), it proceeds to Step S210. When there are left undone some samples (i<m), '1' is added to the 'i' at Step S209 and the steps starting from Step S202 inclusive are performed for the following calibration sample.

At Step S210, the calculated mean values 'Mik' s and standard deviations 'Sik's of the signal intensities in the respective bands are retrieved from the storing unit 210 so as to be displayed in the form of graphs on the display unit 240. A screen example in which they are displayed on the display unit 240 is shown in FIG. 10.

The mean values and standard deviations of the signal intensities per band are displayed in the band intensity information display area 400 on the screen of the display unit 240. In FIG. 10, an example in which there are three kinds of the calibration samples is shown, in which three kinds of graphs are illustrated. In any of those graphs, the vertical axes 401 indicate signal intensities at the respective bands while the transversal axis 402 indicates the band. Rectangular bars 411 respectively indicate the mean value of the signal intensities in the respective bands and the respective linear bars 412 illustrated over the bars 411 indicate the standard deviation of the signal intensities in the corresponding band.

In order to separate fluorescent lights of the respective fluorochromes from one another with high precision, it is very essential that there be a band in which a higher signal intensity is marked with only one of the calibration samples while a lower signal intensity is marked with the other samples and there are a few fluctuations in the signal intensities in the respective bands. As mentioned above, computing the signal intensities and fluctuation (standard deviations) in the respective bands and displaying the results as shown in FIG. 10 allows whether or not the selection of a band is appropriate to be grasped before starting measuring the analyte. Hereupon, it is exemplified that the average wavelength intensity and the standard deviation are calculated for the whole bands, but necessary information may well be picked up according to an object to which the present analytical processing is performed.

Figure 10:
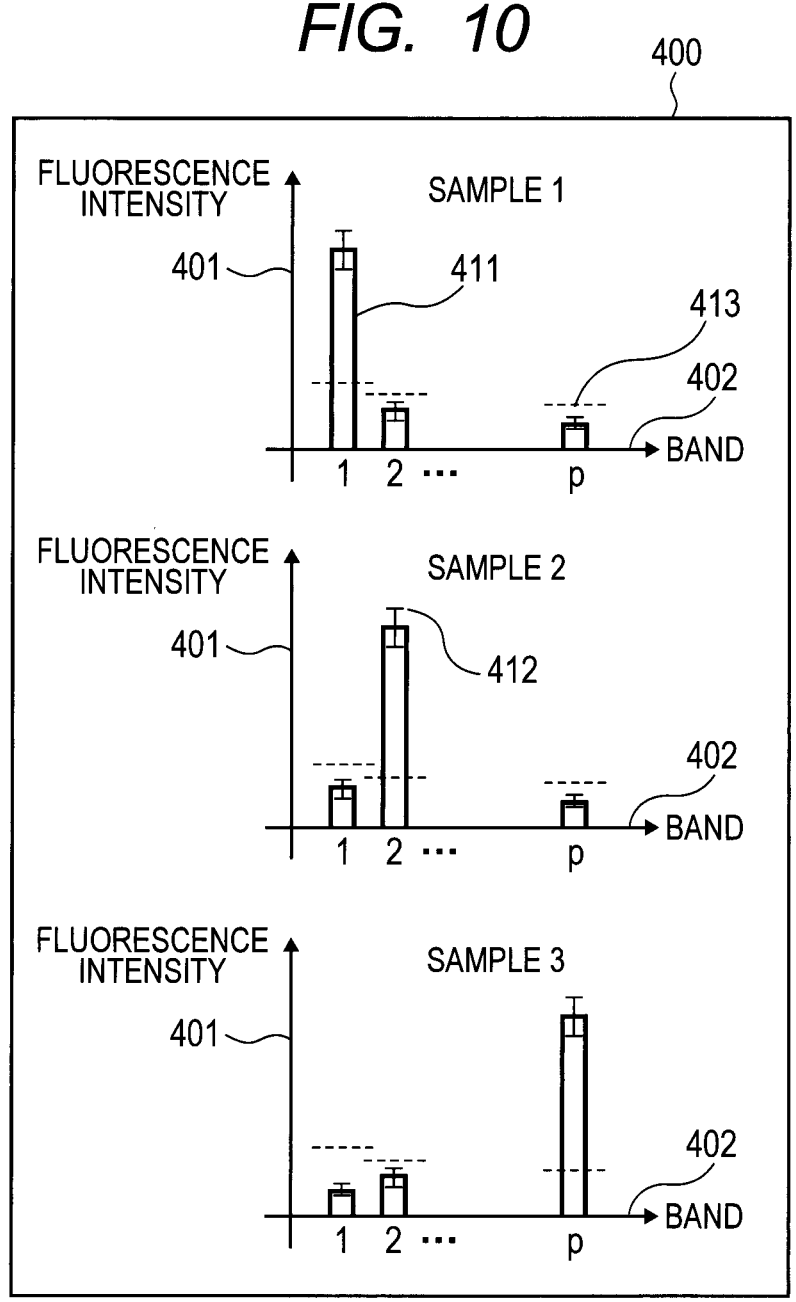
FIG. 10 is a view showing an example of a screen for displaying the mean and the standard deviation of the wavelength band intensity.

As for the example of Step S150 of FIG. 5, the user checks the signal intensities and fluctuations in the respective bands through the screen example illustrated in FIG. 10 and determines whether or not the measurement is performed with the set band of wavelength. When the user determines that resetting such band is required, it returns to Step S130 at which a band of wavelength to be measured is afresh set. When it is not required to reset the same, it proceeds to Step S160.

To note, it is preferred that the band intensity information display area 400 be displayed simultaneously with the average fluorescence spectrum display area 300. Displaying them at the same time allows information on where a band is set and whether or not such set band is appropriate to be simultaneously grasped, which leads to improving on the efficiency with which a band is to be set.

At Step S160, there is shown an example in which the user sets a cutoff value. The cutoff value unit a noise level and the signals at that cutoff value or lower than the same are rejected as noises. The setting of the cutoff value is performed on the band intensity information display area 400 of the screen shown in FIG. 10. It is exemplified herein that different cutoff values are settable for the respective bands and such value is set by clicking a point to which it is desirably set over the rectangular bar 411 indicating the mean value of the signal intensities in the respective bands. A broken line 413 is indicated at the position of the set cutoff value. It is preferred that once a cutoff value is set over any one of the graphs, the broken lines 413 showing such value be indicated also in the other graphs at the same position as that set in the first one. Controlling of the screen for setting the cutoff values and importing of such values set by the user are performed by the cutoff value setting unit 280, and the set cutoff values are stored in the storing unit 210.

It requires that the noise components of the cutoff values be rejected as much as possible and the signals to be desirably measured be rejected as little as possible. As mentioned above, supportively displaying the mean values of the intensities and fluctuations (standard deviations) in the respective bands for the respective calibration samples in the form of graphs on the screen and enabling the cutoff values to be set over the graphs on the screen permits an optimum cutoff value to be set.

Subsequently at Step S170, estimated measurement accuracy information is computed and the result is displayed on the display unit 240. The intensities of the respective particles of the respective calibration samples in the respective bands are distributed within a certain range. Hereupon, as mentioned earlier, the narrower the distributions of the band intensities of the respective calibration samples are as well as the shorter the center-to-center distance between the distributions is, the smaller an error during the measurement is. Thus, regarding the distribution of the band intensities of the calibration sample as probability distribution, an extent to which the respective distributions are overlapped is computed as estimated measurement accuracy information. The smaller such extent is, the higher the precision of the measurement results.

Figure 12:
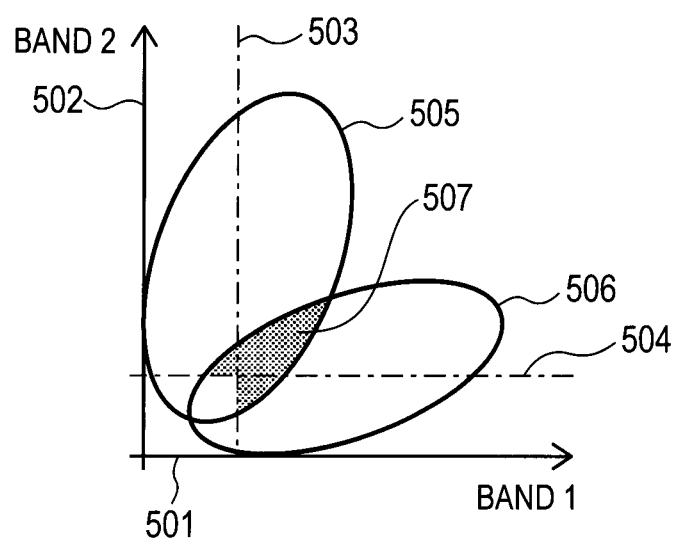
FIG. 12 is a view to explain how to calculate the overlapping of distributions.
Figure 13:
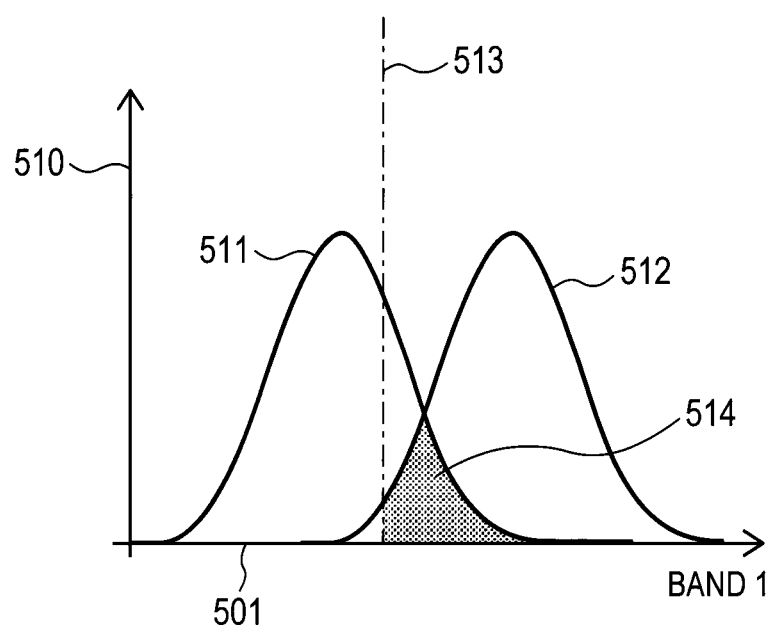
FIG. 13 is a view to explain how to calculate the overlapping of distributions.
Figure 15:
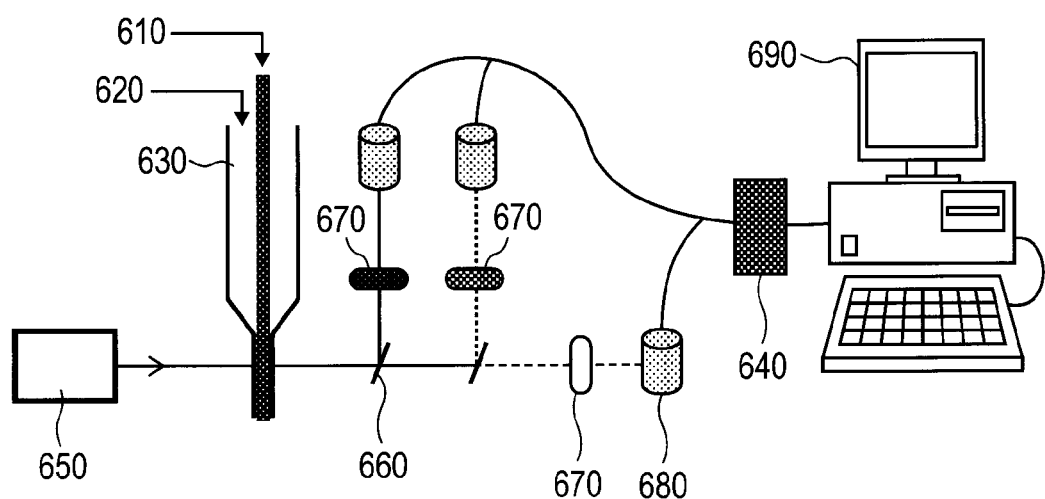
FIG. 15 is a view showing an example of the structural arrangement of the conventional flow cytometer.
Figure 16:
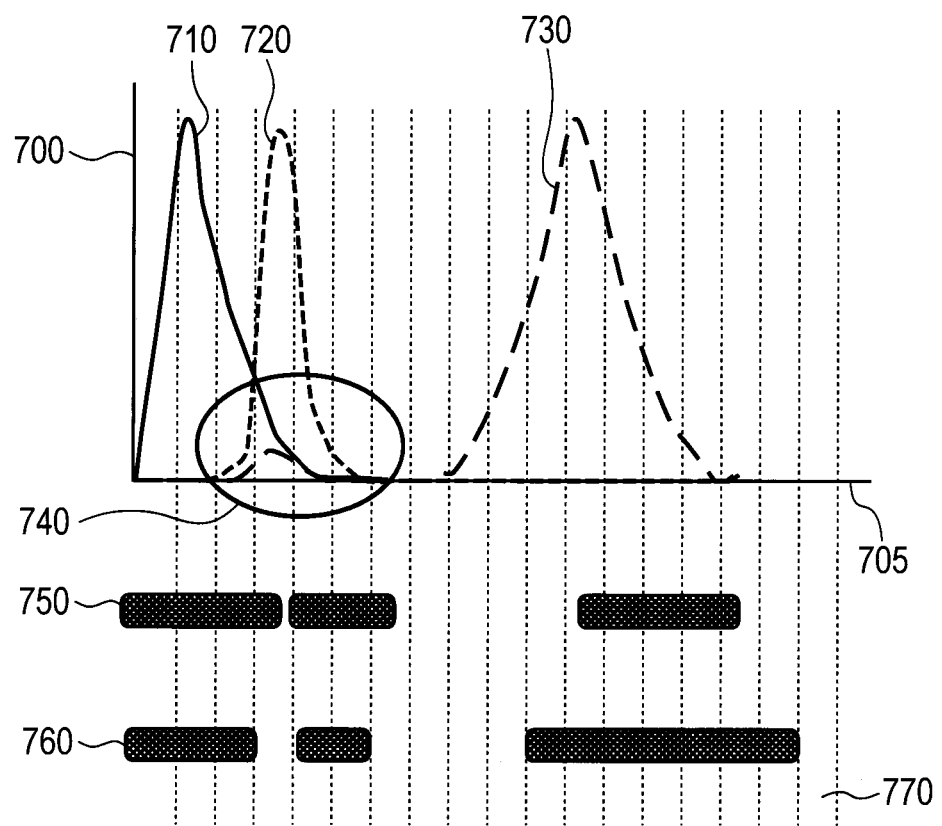
FIG. 16 is a view showing an example in which a wavelength band to be detected is set when a spectroscope and a multi detector are used.

The principle, based on which the overlapping between the distributions is calculated, is explained with reference to FIGS. 12 and 13. In FIG. 12, the transversal axis 501 and the vertical axis 502 indicate the intensity of the bands 1 and 2 respectively. Further, the one-dot chain lines 503 and 504 indicate a cutoff value set in the intensity of the bands 1 and 2 respectively. The oval shapes 505 and 506 indicate an extent to which the distribution of the intensity in the respective bands extends, which extent is computed with reference to the fluorescent lights of the particles contained in the calibration samples 1 and 2 respectively. Hereupon, the region in which the distributions are overlapped turns out to be that 507 with an area rejected by the cutoff values excluded from the overlapping between those oval shapes 505 and 506.

Upon actually calculating the extent to which they are overlapped, the regions indicated with the oval shapes 505 and 506 are expressed as probability distributions. In order to simplify the explanation, the situation in which two probability distributions are overlapped when only one band is chosen (e.g., the band 1 being selected) is shown in FIG. 13. The transversal axis 501 indicates the intensity of the band 1 while the vertical axis 510 indicates probability. The curved lines 511 and 512 indicate the probability distribution of the calibration samples 1 and 2 respectively while a one-dot chain line 513 indicates a cutoff value set in the intensity of the band 1. Hereupon, an area of the region 514 with a portion rejected by the cutoff values excluded from the region where two distributions are overlapped is calculated. The region 514 is actually of multidimensional distribution, so that a multidimensional volume is calculated.

Figure 11:
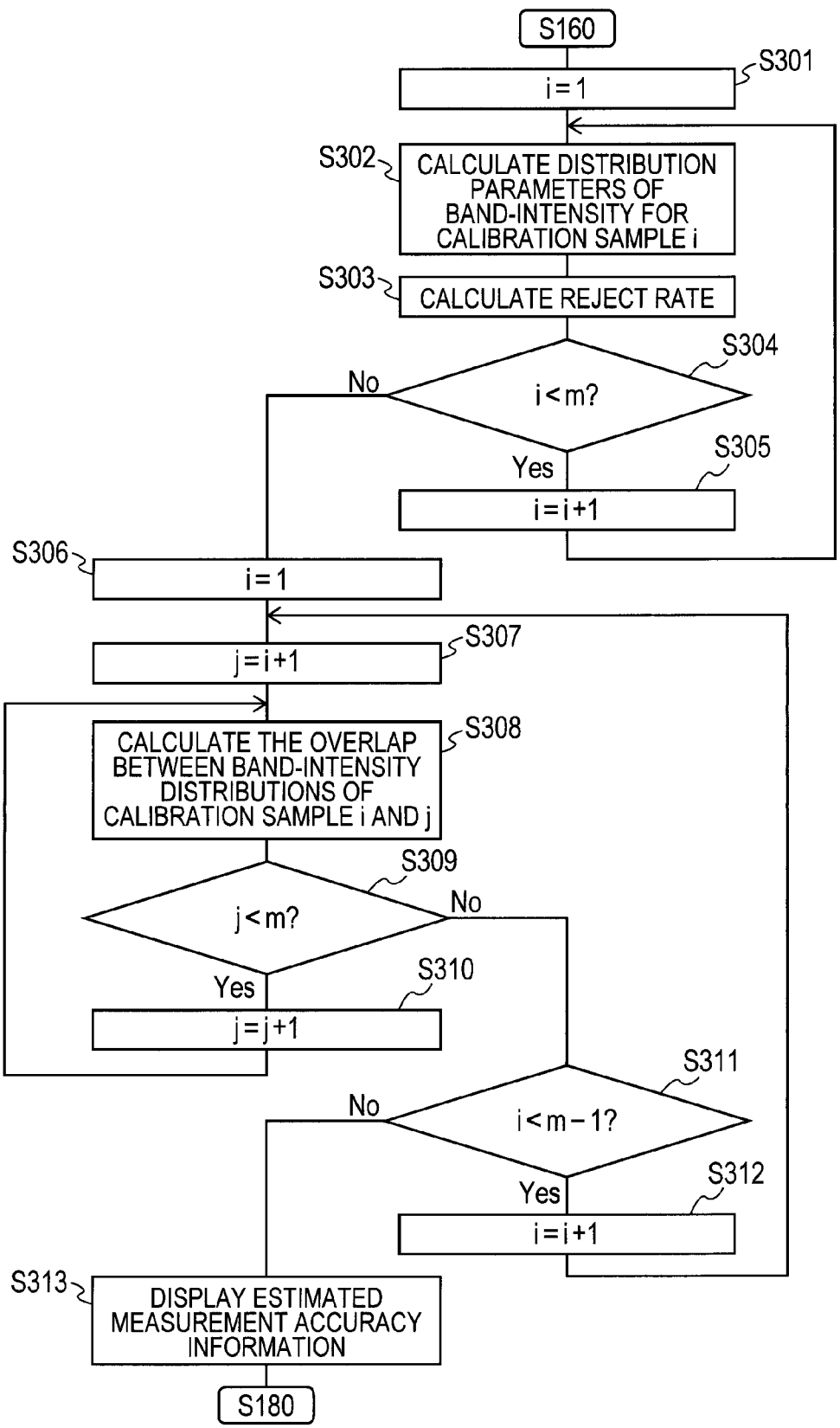
FIG. 11 is a view showing the detailed processing flow for calculating and displaying information on the estimated measurement accuracy.

One example of the detailed processing at Step S180 based on the above principle is explained with reference to FIG. 11. To note, the steps shown in FIG. 11 are performed by the estimated measurement accuracy information calculation unit 270 as shown in FIG. 6. The following explanation is on the basis that the 'm' kinds of the calibration samples are used.

At Steps S301 to S305, a probability distribution indicating the distribution of the intensities in the respective bands as well as a reject rate are calculated for the respective calibration samples, which rate is the proportion of the particles to be rejected as noises by the cutoff value. In the first place, at Step S301, '1' is assigned to the variable 'i' indicating the kind of the calibration sample for initialization. At Step S302, parameters by which the distribution of the intensities in the respective bands derived from the fluorescent lights of the particles of the calibration sample 'i' is matched to the probability distribution are computed. For instance, when a multidimensional normal distribution is adopted for the probability distribution, a variance-covariance matrix is calculated. However, the probability distribution employed herein is not limited to the normal distribution. Any other various probability distributions are adoptable herein. It may well be arranged such that the plurality of probability distributions is available and selectable to the user. To note, the parameters computed herein are stored in the storing unit 210.

Subsequently, at Step S303, the reject rate is calculated, which rate may be calculated as the proportion of the particles rejected by the cutoff value to the whole particles based on the actual data measured on the calibration samples. Further, such rate may well be calculated as an integrated value of the probability distributions for the regions having a higher cutoff value than that of the intensities in the respective bands with the probability distribution calculated at Step S302 in use. The reject rates calculated herein are stored in the storing unit 210.

At Step S304, comparing the variable 'i' with the kinds of the sample 'm, whether or not the steps S302 and S303 have been finished for the whole calibration samples is determined. When such steps have been over for the whole samples (i=m), it proceeds to the Step S306. If in the negative (i<m), after '1' is added to the variable 'i' at Step S305, the steps starting from Step S302 inclusive are taken.

At Steps S306 to S312, an extent to which the probability distributions between two kinds of calibration samples are overlapped is calculated. At Step S306, '1' is assigned to the variable 'i' indicating the kind of one of the calibration samples subjected to the calculation of such extent for initialization. Further, at Step S307, 'i+1' is assigned to the variable 'j' indicating the kind of the other of the calibration samples for initialization.

At Step S308, with the computed parameters on the probability distribution at Step S302 in use, an extent to which the distributions of the signal intensities in the respective bands between the calibration samples 'i' and 'j' are overlapped is calculated based on the principle explained with reference to FIGS. 12 and 13. The calculation results are stored in the storing unit 210. At Step S309, comparing the variable 'j' with the kinds of the sample 'm', whether or not the whole processing of Step S308 has been over for the calibration sample 'i' is determined. When in the affirmative (j=m), it proceeds to Step S311. When there is something left undone (j<m), after '1' is added to the at Step S310, the steps starting from Step S308 inclusive are taken.

At Step S311, comparing the 'i' with 'm−1', whether or not the step, by which an extent to which the distributions of the signal intensities in the respective bands between the whole combinations of the calibration samples are overlapped is calculated, has been taken is determined. If in the affirmative (i=m−1), it proceeds to Step S313. When there is something left undone, after '1' is added to the 'i' at Step S312, the steps starting from Step S307 inclusive are taken.

At Step S313, the computed overlapping extents of the distributions and reject rates are displayed on the display unit 240 as estimated measurement accuracy information. An example in which such information is displayed is shown in FIG. 14. This example is illustrated in the form of matrix, in which a value of the cell over which the rows of 'Sample i' and the columns of 'Sample j' run crosswise indicates an extent to which the probability distributions are overlapped between the samples and 'j'. Further, reject rates are displayed at the lowest row.

Then, at Step S180 of FIG. 5, the user considers whether or not the cutoff values are to be reset with reference to the estimated measurement accuracy information. When it is determined that they shall be reset, it returns to Step S160 in which such values are reset. When the cutoff value is not reset, at Step S190, the user considers whether or not the wavelength bands shall be reset. If in the affirmative, it returns to Step S130 in which such bands are to be reset. If in the negative, the bands to be measured are finalized at Step S104.

To note, it is preferred that the estimated measurement accuracy information be displayed on the display unit 240 along with the average fluorescence spectrum display area 300 and the band intensity information display area 400. Displaying the estimated measurement accuracy information allows the user to grasp whether or not the set bands are appropriate quantitatively or from the extent to which the distributions are overlapped, which supports the user to set optimum bands for more accurate measurement.

At those steps shown in FIG. 5, it may well be arranged such that the user can select the respective steps in accordance with measurement conditions imposed by the user or the required precision. Further, it may well be arranged such that the user can select fluorescent lights subjected to computation at the respective steps and detectors as well as calculation methods in accordance with such conditions and precision.

Figure 21:
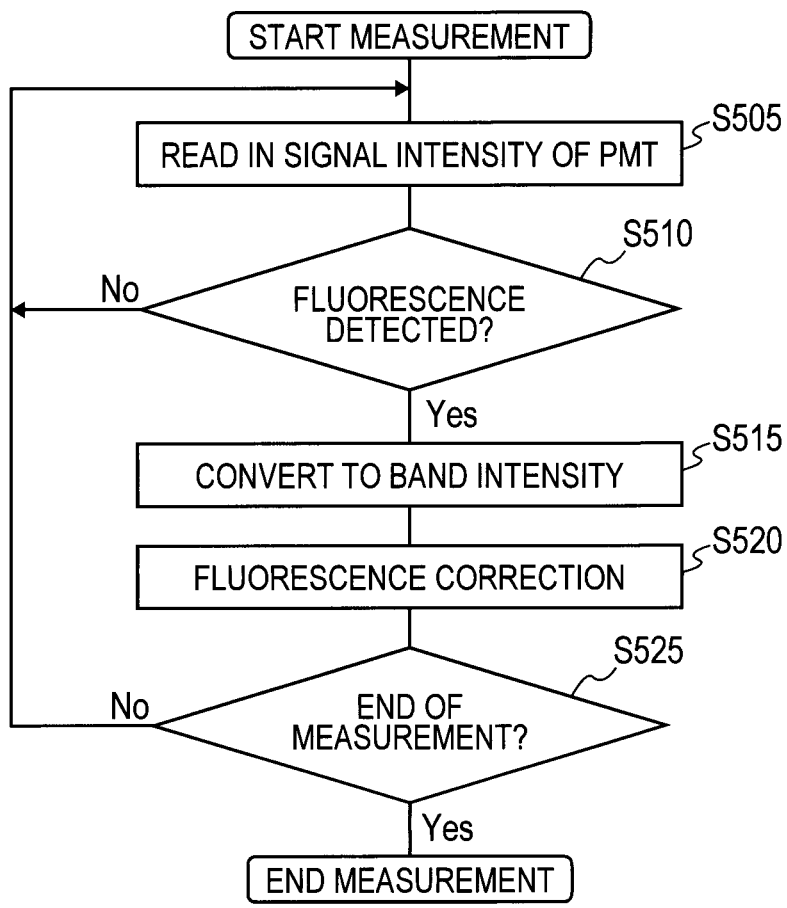
FIG. 21 is a view showing the processing flow for measuring an analyte.

Then, the processing flow of measuring an analyte at Step S105 is in detail explained with reference to FIG. 21. Upon such analyte being measured, the user places the analyte preliminarily subjected to fluorescent labeling on the apparatus and instructs measurement to start. The instruction to start the measurement is carried out with a keyboard coupled to the signal processing unit 106, for instance. Upon the measurement being instructed, the signal processing unit 106 imports the signal intensity data of the PMT outputted from the A/D converter (Step S505) so as to determine whether or not fluorescent light is detected (Step S510). For example, threshold values are predetermined for the whole channels of the PMT and when the output value of at least one of the channels is larger than such threshold value, it is determined that fluorescent light has been detected. When such light has not been detected, it returns to Step S505 in which the signal intensity of the PMT is afresh imported.

When fluorescent light has been detected at Step S510, a signal intensity is converted into a band intensity at Step S515. More concretely, bands set by the user at Step S104 are imported from the storing unit 210 and the signal intensities of the plural channels are added according to the set bands so as to be turned into a band intensity. Further, at the same time, it may well be arranged such that the cutoff values set by the user at Step S160 are imported from the storing unit 210 and the particles whose band intensities as a whole are smaller than the cutoff values are rejected. When such reject is carried out, the subsequent steps from Step S520 inclusive are not taken, but the steps from Step S505 inclusive are afresh taken. Further, there may well be no need that such particles are rejected with such cutoff values in use. In this case, it may well be arranged such that the bands intensities of the respective particles are in a while stored in the storing unit and such reject operation with such values in use and fluorescence correction are carried out with another software after the end of the measurement.

At Step S520, an example in which fluorescence correction is performed for the bands intensities computed at Step S515 is shown. The relationship between the bands intensities computed at Step S515 and the distributions of the intensities of the particles contained in the actual analyte is shown in FIG. 20 (A), for example. That is to say, the distributions of the bands intensities of the particles contained in the same analyte have a certain inclination within a coordinate space interposed between the axes of such bands intensities. At the fluorescence correction at Step S520, such inclination is converted into new coordination axes. More concretely, the directions to which the respective distributions extend are calculated according to multivariate statistics and coordinate conversion is performed in which new axes are established along such directions. At this time, the parallel shifting of the respective coordinate axes is also carried out lest that the bands intensities of the respective particles represented in the converted coordinate system become negative numbers.

Figure 22:
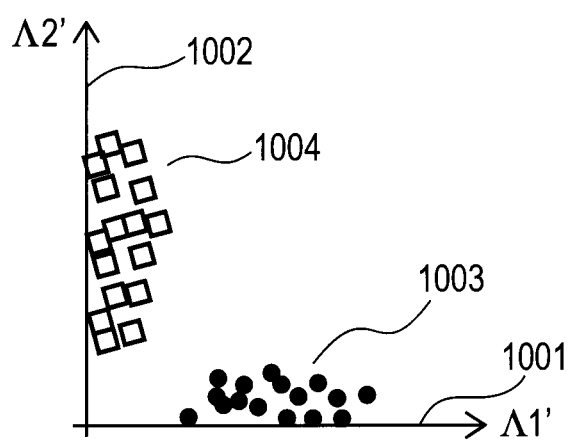
FIG. 22 is a view showing the band intensity distribution of the particles in the analyte after fluorescence correction.

The exemplary view of the distributions of the bands intensities of two kinds of particles contained in the sample after the fluorescence correction is shown in FIG. 22. The transversal axis 1001 and the vertical axis 1002 indicate a band intensity Λ1' and that Λ2' newly established after the fluorescence correction. The numerical references 1003 and 1004 indicate the band intensities of fluorescent lights emitted from different kinds of particles contained in the analyte.

In this way, converting the illustration shown in FIG. 20 (A) into the state shown in FIG. 22 through the fluorescence correction permits the band intensity Λ1' to be equal to the light emitting intensity of Sample 1 (fluorochrome 1): (Band intensity Λ1')=(Light emitting intensity of Sample 1 (fluorochrome 1), which makes it possible to represent the light emission of one kind of fluorochrome with the single intensity.

According to the present invention, it allows optimum channels to be selected and optimum cutoff values to be set, which minimizes the overlapped region between the distributions of the intensities in different kinds of bands so as to result in the measurement with high precision.

At Step S525, whether or not the measurement ends is determined. If in the negative, it returns to Step S505. To note, whether or not it ends may well be determined based on the lapse of time from the measurement start, in which it ends when a certain time has lapsed from such start. Further, it may well end when the remaining amount of the analyte has reached a certain value or less with the same monitored. Furthermore, it may well end when the measured amount of the analyte has gone beyond the predetermined amount thereof with the same monitored.

With the flow cytometer as mentioned above, calculating the spectra of the calibration sample and displaying the same allows the wavelength bands to be appropriately set with intrinsic fluorescence and a peak shift taken into account upon such bands being set at the measurement. Further, calculating information on the distributions of the signal intensities for the respective set bands and displaying the same permits information on precision in measurement to be obtained before the analyte is subjected to such measurement, which supports the user to select optimum bands and to set cutoff values matching the purposes for such measurement. Furthermore, calculating an extent to which the distributions of the intensities in the set bands between the calibration samples are overlapped and displaying the same allows the user to qualitatively grasp precision at the measurement, which supports the user to select optimum bands.

Second Embodiment

In the present embodiment, another example of the method for calculating and displaying measured intensity information for the bands of wavelength at Step S140 of FIG. 5 explained in the first embodiment is described. The other steps are the same as those of the first embodiment, so that their explanations are omitted.

At Step S140, the intensities in the respective set bands are computed for the detected whole particles of the respective calibration samples. The intensities in the respective bands are calculated as the sum of the intensities (those measured by one channel of the PMT) of the wavelengths included in such respective bands. The calculated intensities in the respective bands are stored in the storing unit 210.

Figure 17:
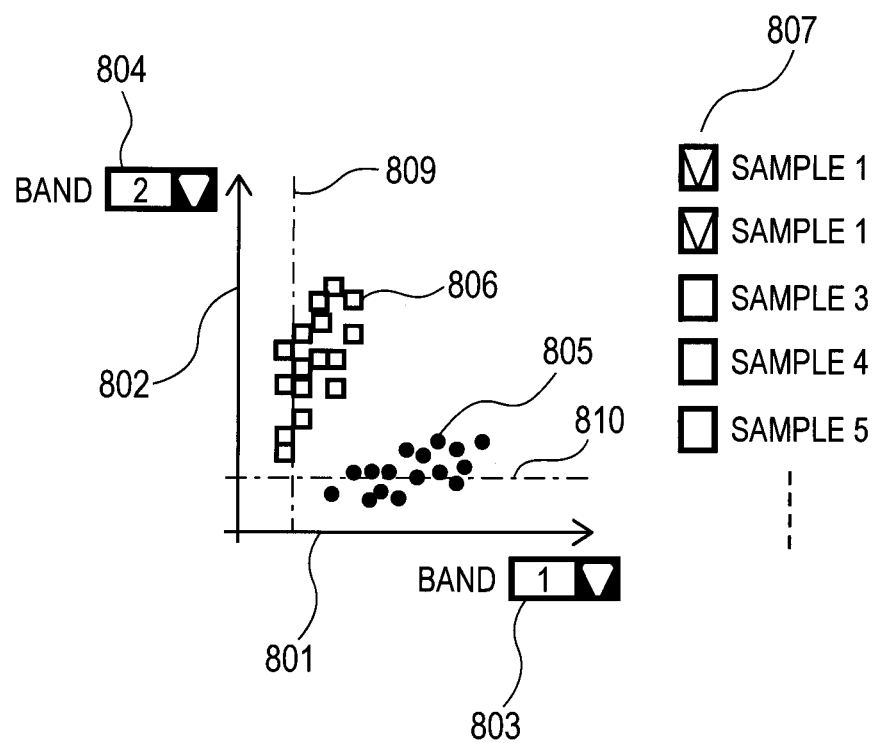
FIG. 17 is a view showing an example of the screen in which bands intensities distributions are displayed.

Then, in the band intensity information display area 400 of the display unit 240, a screen shown in FIG. 17 is displayed. In this screen, the distributions of the intensities in the respective bands of the selected calibration samples are retrieved from the storing unit 210 so as to be displayed on the coordinate plane in which arbitrary two kinds of bands are placed in the transversal and vertical axes.

The reference numeral 803 indicates a list box from which a number of the band placed on the transversal axis is selected while that 804 indicates a list box from which that of the band placed on the vertical axis is selected. The user selects the numbers of the bands whose distributions of the intensities are to be checked. In an example shown in FIG. 17, Band 1 is placed on the transversal axis 801 while Band 2 is placed on the vertical axis 802. The reference numeral 807 is a check box from which the number of the calibration samples whose distributions of the intensities are to be displayed on the coordinate is selected. The user selects the calibration sample whose distributions are to be checked by clicking the mouse. In an example shown in FIG. 17, Samples 1 and 2 are selected.

According to the above operations, the distributions of the intensities in the respective bands of the selected samples are displayed. In an example shown in FIG. 17, the distributions 805 of the intensities in the respective bands of Sample 1 and those 806 of Sample 2 are displayed on the coordinate in which the intensity of Band 1 is placed on the transversal axis 801 while that of Band 2 is placed on the vertical axis 802.

Further, in the present embodiment, the setting of the cutoff values explained at Step S160 of FIG. 5 is performed on the screen shown in FIG. 17. Clicking the positions along the transversal axis 801 and the vertical axis 802 to which the user wishes to set such values allows values corresponding to such positions to be set as the cutoff values. Further, the lines corresponding to the set cutoff values are displayed on the coordinate. In an example shown in FIG. 17, a one-dot chain line 809 indicates a cutoff value set for the intensity of Band 1 while a one-dot chain line 810 indicates that set for the intensity of Band 2.

In the above second embodiment, displaying the distributions of the intensities in the respective bands on the coordinate axes allows the shape and extent of such distributions of the intensities of the respective calibration samples as well as an extent to which the distribution of the one sample is overlapped with that of the other sample to be visually grasped, which facilitates whether or not the set bands are appropriate to be determined and such cutoff values to be set.

Third Embodiment

In the third embodiment, another example of the method for calculating and displaying estimated measurement accuracy information at Step S170 of FIG. 5 explained in the first embodiment is described. The other steps are the same as those of the first embodiment, so that their explanations are omitted.

Figure 18:
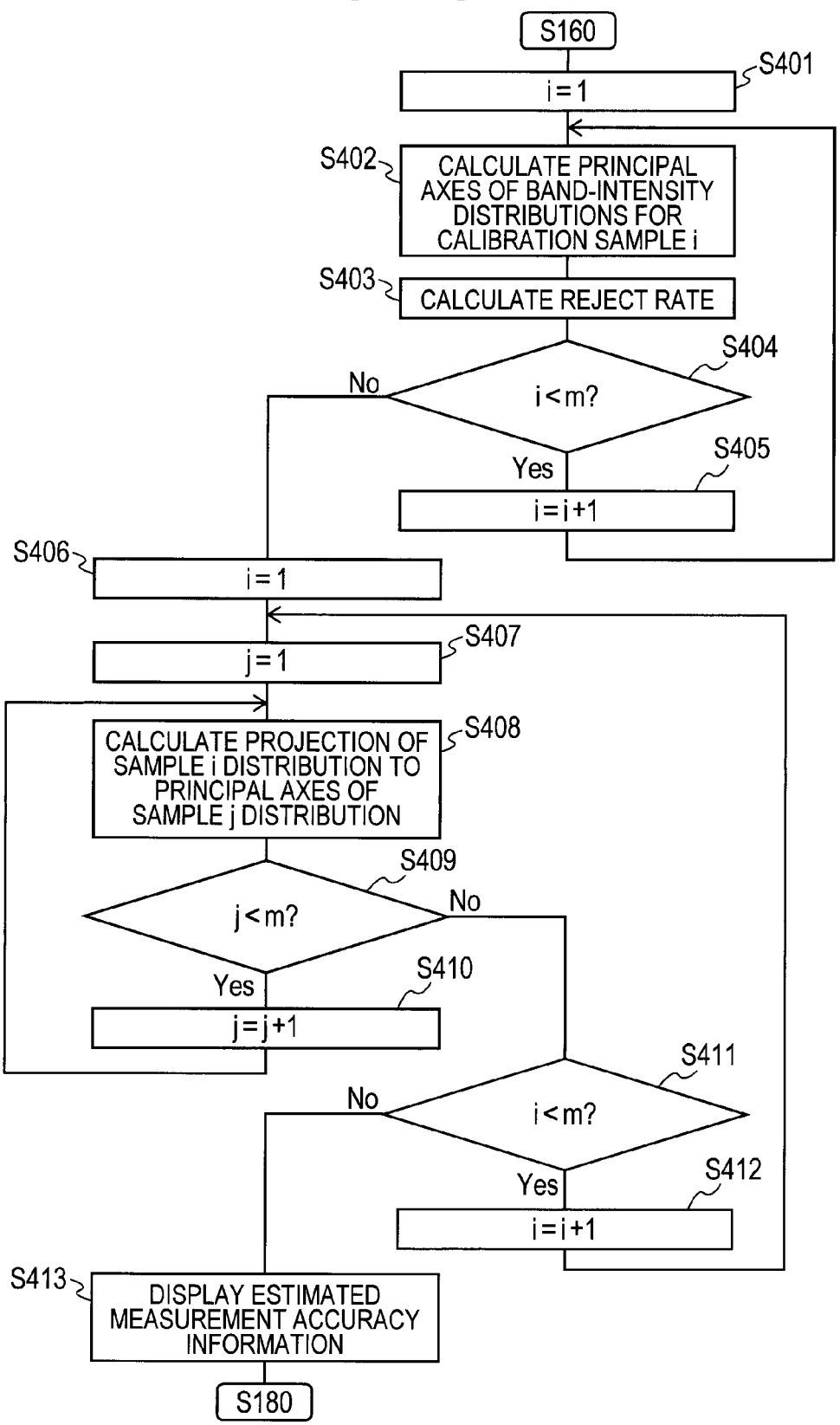
FIG. 18 is a view showing the detailed processing flow for calculating and displaying the estimated measurement accuracy information.

In FIG. 18, the detailed processing flow of Step S170 is shown according to the present embodiment, which processing is performed by the estimated measurement accuracy information calculation unit 270 shown in FIG. 6. To note, the following explanation is provided that it uses 'm' kinds of the calibration samples.

At Steps S401 to S405, the principal axes of the distributions of the intensities in the respective bands of the respective calibration samples as well as the reject rates are calculated. The reject rate is the proportion of the particles to be rejected by the cutoff value as noises. In the first place, at Step S401, '1' is assigned to the variable indicating the kind of the calibration sample for initialization. At Step S402, the principal axis of the distributions of the intensities in the respective bands of the calibration sample 'i' derived from the fluorescent lights of its particles is calculated. The principal axis is a line showing the direction having the largest extent in case where the distribution of the intensities is regarded as the multidimensional normal distribution, which axis can be calculated by multivariate statistics. The calculated principal axis is stored in the storing unit 210.

Then, at Step S403, the reject rate is calculated, which rate can be calculated as the proportion of the particles rejected by the cutoff value to the whole particles based on the actual data measured on the calibration sample. The calculated reject rate is stored in the storing unit 210.

At Step S404, comparing the variable 'i' with the kinds of the sample 'm', whether or not the steps S402 and S403 have been over for the whole calibration samples is determined. If in the affirmative (i=m), it proceeds to Step S406. If in the negative (i<m), after '1' is added to the 'i' at Step S405, the subsequent steps from Step S402 inclusive are taken.

At Steps S406 to S412, an influence that the intensities of a certain calibration sample give to those of the other samples is calculated. At Step S406, '1' is inserted for initialization into the variable 'i' indicating the kind of one of the calibration samples whose extent to which the distributions of the intensities are overlapped with those of the other is calculated. Further, at Step S407, '1' is assigned to the variable 'j' indicating the other kind of the calibration samples for initialization.

At Step S408, with the principal axis calculated at Step S402 in use, components of projection of the distributions of the intensities of the calibration sample 'i' to the principal axis of those of the calibration sample 'j' are calculated and the distribution of such components is calculated. For instance, the mean value and standard deviation of such components are calculated. The principle based on which such components are calculated is shown in FIG. 20. The transversal axis 901 and the vertical axis 402 respectively indicate the intensity of Band 1 and that of Band 2. In FIG. 20 (A), the reference numeral 903 indicates the intensities in Bands 1 and 2 derived from the fluorescent lights emitted from the respective particles of the sample 'i' while that 904 indicates the fluorescence intensities of the respective particles of the sample 'j'. Further, the line 905 indicates the principal axis of the distributions of the intensities in the respective bands of the sample 'i' while that 906 indicates the principal axis of the distributions of the intensities in the respective bands of the sample 'j' as calculated at Step S402. Hereupon, as shown in FIG. 20 (B), the foots of the vertical lines 907 drawn to the principal axis 906 of the distributions in the intensities of the sample 'j' from the respective points of the distributions of the intensities in the respective bands of the sample 'i' indicate such components of projection. That is to say, the distances between the intersecting points of the vertical lines with the principal axis 906 and the origin of the coordinate result in such components. The components of projection with regard to the principal axis 906 for the respective particles of the sample 'i' are computed and the distribution of the computed components of projection is calculated. The curved line 908 shows the shape of the calculated distribution. For instance, the mean value and standard deviation of this distribution are calculated.

The calculated results are stored in the storing unit 201. At Step S409, comparing the sample 'j' with the kinds of the sample 'm', whether or not the whole processing of Step S408 has been over for the calibration sample 'i' is determined. If in the affirmative (j=m), it proceeds to Step S411. If in the negative (j<m), after '1' is added to the sample 'j', the subsequent steps from Step S408 inclusive are taken.

At Step S411, comparing the sample 'i' with the kinds of the sample 'm', whether or not the step, by which an extent to which the distributions of the signal intensities in the respective bands between the whole combinations of the calibration samples are overlapped is calculated, has been taken is determined. If in the affirmative (i=m), it proceeds to Step S413. If in the negative, after '1' is added to the sample 'i' at Step S412, the subsequent steps from Step S407 inclusive are taken.

At Step S413, the computed components of projection with regard to the principal axis and the reject rates are displayed on the display unit 240 as estimated measurement accuracy information. An example in which such information is displayed is shown in FIG. 19. It is illustrated with a matrix, in which a value of the cell over which the rows of 'Sample i' and the columns of 'Sample j' run crosswise indicates the shape of the distribution of components of projection of the distribution of the intensities of the sample 'i' towards the principal axis of the distribution of the intensities of the sample 'j'. For instance, the shape of the distribution of such components is displayed in the expression of mean value±standard deviation. Further, the reject rates are displayed at the lowest row.

The components of projection of the distribution of the intensities of the calibration sample directed towards the principal axis represent the light emitting intensity of fluorochromes added to such sample. Thus, the components of projection of the distribution of the intensities of the other calibration samples directed towards such axis in the same way give an influence as error components at the time of carrying out multiple stain measurement. The present embodiment permits a mutual influence to the components of projections of the calibration samples to be quantitatively grasped and mutual error among the samples upon the measurement being carried out with multiple stain to be preliminarily estimated, which supports the user to select optimum bands before starting the measurement.

LIST OF REFERENCE SIGNS

101: laser
102: flow cell
103: spectral device
104: Photo-multiplier tube (PMT)
105: A/D converter
106: Signal processing unit
111: Axis indicating fluorescence intensity
112: Axis indicating wavelength
113: Curved line indicating fluorescence spectrum
114: Curved line indicating fluorescence spectrum
115: Range of frequencies $\Lambda 1$
116: Range of frequencies $\Lambda 2$
121: Axis indicating intensity of wavelength $\lambda 3$
122: Axis indicating intensity of wavelength $\lambda 14$
123: Reference numeral indicating distribution of signals measured upon fluorochrome A emitting light
124: Reference numeral indicating distribution of signals measured upon fluorochrome B emitting light
125: Axis indicating intensity of wavelength band $\Lambda 1$
126: Axis indicating intensity of wavelength band $\Lambda 2$
127: Broken line indicating direction to which distributions of signals measured upon fluorochrome A emitting light
128: Broken line indicating direction to which distributions of signals measured upon fluorochrome B emitting light
210: Storing unit
220: Fluorescence spectrum obtaining unit
230: Spectrum information calculation unit
240: Display unit
250: Band-setting unit
260: Wavelength intensity calculation unit
270: Estimated measurement accuracy information calculation unit
280: Cutoff value setting unit
300: Average fluorescence spectrum display area
301: Average fluorescence spectrum of particles of sample 1
302: Average fluorescence spectrum of particles of sample 2
303: Average fluorescence spectrum of particles of sample 3
311: Bar indicating standard deviation
320: Band-setting area
321: Arrow indicating band 1
322: Arrow indicating band 2
323: Arrow indicating band 3
400: Band intensity information display area
401: Axes indicating fluorescence intensity of respective bands
402: Axis indicating band 411: Bar indicating mean value of fluorescence intensity in respective bands
412: Bar indicating standard deviation of fluorescence intensity in respective bands
413: Broken line indicating cutoff value
501: Axis indicating signal intensity of band 1
502: Axis indicating signal intensity of band 2
503: One-dot chain line indicating cutoff value set for intensity of band 1
504: One-dot chain line indicating cutoff value set for intensity of band 2
505: Oval shape indicating band intensity distribution range of calibration sample 1
506: Oval shape indicating band intensity distribution range of calibration sample 2
507: Region indicating overlapping of distributions
510: Axis indicating probability
511: Probability distribution of calibration sample 1
512: Probability distribution of calibration sample 2
513: One-dot chain line indicating cutoff value set for intensity of band 1
514: Region indicating overlapping of distributions
610: Fluorescence-stained sample
620: Sheath solution
630: Flow cell
640: Electric signal processing section
650: laser beam
660: Dichroic mirror
670: Band path filter
680: Photo-multiplier tube (PMT)
690: Exclusive software
700: Axis indicating fluorescence intensity
705: Axis indicating wavelength
710: Curved line indicating fluorescence spectrum
720: Curved line indicating fluorescence spectrum
730: Curved line indicating fluorescence spectrum
740: Region indicating overlapping of fluorescence spectra
750: Wavelength bands to be detected set by conventional system
760: wavelength bands to be detected set with spectral device and multi detector in use
770: Wavelength bands detected by one detector
801: Axis indicating band intensity
802: Axis indicating band intensity
803: List box for selecting band number
804: List box for selecting band number
805: Reference numeral indicating distribution of band intensities of sample 1
806: Reference numeral indicating distribution of band intensities of sample 2
807: Check box for selecting kind of sample
809: One-dot chain line indicating cutoff value
810: One-dot chain line indicating cutoff value
901: Axis indicating signal intensities of band 1
902: Axis indicating signal intensities of band 2
903: Reference numeral indicating distribution of band intensities of sample 1
904: Reference numeral indicating distribution of band intensities of sample 2
905: Principal axis of distribution of signal intensities of sample 1
906: Principal axis of distribution of signal intensities of sample 2
907: Vertical line drawn to principal axis of distribution of signal intensities of sample 2 from those of sample 1
908: Curved line indicating shape of distribution of components of projection of signal intensities of sample 1 towards the principal axis of signal intensities of sample 2
1001: Axis indicating band intensity after fluorescence correction
1002: Axis indicating band intensity after fluorescence correction
1003: Reference numeral indicating band intensity distribution of fluorescent lights emitted by particles contained in analyte after fluorescence correction
1004: Reference numeral indicating band intensity distribution of fluorescent lights emitted by particles contained in analyte after fluorescence correction

The invention claimed is:

1. An analytical apparatus comprising:
a light source;
a flow cell to flow a sample receiving light from the light source and emitting light;
a spectral device to diffract the light emitted from the sample;
a detection section provided with a plurality of detectors to detect the diffracted light outputted from the spectral device per different wavelength;
a processor including a signal processing unit configured to process a signal of the light detected by the detection section;
an input unit configured to input an instruction for the signal processing;
a memory, coupled to the processor, configured to store a result of the processed signal; and
an output section to display the result;
the processor further including
a band-setting unit configured to set a wavelength band to be detected by at least one of the detectors through the input unit,
a wavelength intensity calculation unit configured to calculate the intensity of the signal of the detected light in the wavelength band set by the band-setting unit; and to store the intensity for the respective samples into the storage section;
a cutoff value setting unit configured to output the intensity of the signal of the detected light of the wavelength band for the respective samples, which intensity is stored in the storage device with the wavelength intensity calculation unit, to the output section; to make the input unit set a certain value of the intensity based on which the signal whose intensity lower than such certain value inclusive is rejected; and to store the set value of the intensity into the storage section; and
an estimated measurement accuracy calculation unit configured to calculate a reject rate according to the value of the intensity set through the cutoff value setting unit so as to store the reject rate into the storage section; to exclude a rejected portion of the wavelength band set by the band-setting unit; to calculate an extent to which distributions of the intensities in the wavelength bands between a first sample and a second sample among the samples are overlapped; and to output the extent to the output section;
wherein the memory stores the signal of the detected light on a plurality of the samples different from each other in the respective detectors and an intensity of the signal of the detected light at the respective detectors for the respective samples is displayed on the output section.

2. An analytical apparatus comprising:
a light source;
a flow cell to flow a sample receiving light from the light source and emitting light;
a spectral device to diffract the light emitted from the sample;
a detection section provided with a plurality of detectors to detect the diffracted light outputted from the spectral device per different wavelength;
a processor including a signal processing unit configured to process a signal of the light detected by the detection section;
an input unit configured to input an instruction for the signal processing;
a memory, coupled to the processor, configured to store a result of the processed signal; and
an output section to display the result;
the processor further including a band-setting unit configured to set a wavelength band to be detected by at least one of the detectors through the input unit;
wherein the memory stores the signal of the detected light on a plurality of the samples different from each other in the respective detectors and an intensity of the signal of the detected light at the respective detectors for the respective samples is displayed on the output section;
wherein the signal processing unit is configured to calculate a principal axis of the first sample among the respective samples and distribution of components of projection of the distribution of the intensities of the second sample among the respective samples in a direction of the principal axis of the first sample so as to store the principal axis and the distribution of components of projection into the storage section, wherein the output section outputs the distribution of components of projection.

3. An analytical method making use of a light source; a flow cell to flow a sample; a spectral device to diffract light emitted from the sample receiving light from the light source and flowing through the flow cell; a plurality of detectors to detect the diffracted light outputted from the spectral device per different wavelength; a processor configured to process a signal of the light detected by the detectors; a memory configured to store data an input unit configured to provide an input to the processor; and an output section to output the processed result,
wherein the memory stores the signals of the light detected on a plurality of the samples different from each other flowed through the flow cell for the respective detectors, the method comprising:
displaying an intensity of the signal of the detected light at the respective detectors for the respective samples;
setting a wavelength band to be detected by at least one of the detectors through the input unit;
storing the set wavelength band in the memory;
detecting light from an analyte flowing through the flow cell with the detectors;
outputting a signal of the analyte to the output section with the set wavelength band in use;
outputting intensities of the signals of the detected lights in the set wavelength bands for the respective samples to the output section; and
making the input unit input a certain value of the intensity for the outputted signals of the detected lights based on which the signal whose intensity lower than such certain value inclusive is rejected; and storing the value of the intensity into the storage section;
wherein the signal processor performs the steps of:
calculating a reject rate according to the value of the intensity;
excluding a rejected portion of the set wavelength band;
calculating an extent to which distributions of the intensities in the wavelength bands between a first sample and a second sample among the samples are overlapped; and
outputting the extent to the output section.

4. An analytical method making use of a light source; a flow cell to flow a sample; a spectral device to diffract light emitted from the sample receiving light from the light source and flowing through the flow cell; a plurality of detectors to detect the diffracted light outputted from the spectral device per different wavelength; a processor configured to process a signal of the light detected by the detectors; a memory to store data an input unit configured to do an input to the processing unit; and an output section to output the processed result,
wherein the memory stores the signals of the light detected on a plurality of the samples different from each other flowed through the flow cell for the respective detectors, the method comprising:
displaying an intensity of the signal of the detected light at the respective detectors for the respective samples;
setting a wavelength band to be detected by at least one of the detectors through the input unit;
storing the set wavelength band in the memory;
detecting light from an analyte flowing through the flow cell with the detectors;
outputting a signal of the analyte to the output section with the set wavelength band in use;
calculating a principal axis of the first sample among the respective samples and distribution of components of projection of the distribution of the intensities of the second sample among the respective samples in a direction of the principal axis of the first sample so as to store the principal axis and the distribution of components of projection into the storage section; and
outputting the distribution of components of projection to the output section.

* * * * *